(12) United States Patent
Park et al.

(10) Patent No.: US 9,296,690 B2
(45) Date of Patent: Mar. 29, 2016

(54) METHOD FOR INHIBITING DIFFERENTIATION OF OSTEOCLAST AND PHARMACEUTICAL COMPOSITION COMPRISING THEREOF

(71) Applicant: Metacine, Inc., Wonju-si, Gangwon-do (KR)

(72) Inventors: Bae Keun Park, Wonju-si (KR); Sung-Hwa Yoon, Suwon-si (KR); Ju-Young Park, Suwon-si (KR); Sung Hoon Park, Gunpo-si (KR)

(73) Assignee: METACINE, INC., Wonju (KR)

( * ) Notice: Subject to any disclaimer, the term of this patent is extended or adjusted under 35 U.S.C. 154(b) by 0 days.

(21) Appl. No.: 14/293,879

(22) Filed: Jun. 2, 2014

(65) Prior Publication Data

US 2014/0275203 A1      Sep. 18, 2014

Related U.S. Application Data

(63) Continuation-in-part of application No. 13/664,173, filed on Oct. 30, 2012, now abandoned.

(30) Foreign Application Priority Data

Jul. 27, 2012   (KR) .................. 10-2012-0082248

(51) Int. Cl.
```
A61K 31/4015    (2006.01)
C07D 207/448    (2006.01)
C07D 207/452    (2006.01)
C07D 207/38     (2006.01)
C07D 207/444    (2006.01)
C07D 409/04     (2006.01)
C07D 207/20     (2006.01)
C07D 207/408    (2006.01)
C07D 207/456    (2006.01)
```

(52) U.S. Cl.
CPC ........ *C07D 207/448* (2013.01); *A61K 31/4015* (2013.01); *C07D 207/20* (2013.01); *C07D 207/38* (2013.01); *C07D 207/408* (2013.01); *C07D 207/444* (2013.01); *C07D 207/452* (2013.01); *C07D 207/456* (2013.01); *C07D 409/04* (2013.01)

(58) Field of Classification Search
CPC .................................. A61K 31/4015
See application file for complete search history.

(56) References Cited

PUBLICATIONS

Plotkin et al. (Bone, 39 (2006), p. 443-452).*
Park et al. (Toxicology Lett., 120 (2001), 281-91).*
Wermuth, The Practice of Medicinal Chemsitry, 2d ed. (2003), 768 pages. Chs. 9-10 provided.*
Kubinyi (3D QSAR in Drug Design: Ligand-Protein Interactions and Molecular Similarity, vol. 2-3, Springer, 1998, 800 pages). pp. 243-244 provided.*
Zhang et al. (J. Med. Chem. 2010, 53, 5108-5120).*
Sortino et al. (Bioorg. Med. Chem. 19 (2011) 2823-2834).*
Kenjiro Onimura et al., Synthesis and Fluorescent Properties of Model Compounds for Conjugated Polymer Containing Maleimide Units at the Main Chain, Journal of Polymer Science, Part A: Polymer Chemistry (2011), 49(16), 3550-3558.
Manojit Pal et al., A Rapid and Direct Access to Symmetrical/unsymmetrical 3,4-diarylmaleimides and Pyrrolin-2-ones, Tetrahedron (2004), 60(18), 3987-3997.

* cited by examiner

*Primary Examiner* — Robert Havlin
(74) *Attorney, Agent, or Firm* — Novick, Kim & Lee, PLLC; Jae Youn Kim

(57) ABSTRACT

The present invention is for method of treating metabolic bone disease, new compounds and pharmaceutical compositions comprising the active ingredients having inhibition effects on osteoclast differentiation. The pharmaceutical composition comprising new compounds according to the present invention can be used as medicines for treating metabolic bone diseases such as bone metastatic cancer, solid cancer bone metastasis, musculoskeletal complication by solid cancer bone metastasis, hypercalcemia by malignant tumor, multiple myeloma, primary bone tumor, osteoporosis, rheumatoid arthritis, osteoarthritis, periodontal disease, inflammatory resorption of alveolar bone, inflammatory resorption of bone, and Paget's disease.

3 Claims, 5 Drawing Sheets

METHOD FOR INHIBITING DIFFERENTIATION OF OSTEOCLAST AND PHARMACEUTICAL COMPOSITION COMPRISING THEREOF

CROSS-REFERENCES TO RELATED APPLICATION

This patent application is a Continuation-in-part application of U.S. Ser. No. 13/664,173 filed on Oct. 30, 2012, and the contents of which are incorporated herein by reference in its entirely. This patent application claims the benefit of priority from Korean Patent Application No. 10-2012-0082248 filed on Jul. 27, 2012, the contents of which are incorporated herein by reference.

BACKGROUND OF THE INVENTION

1. Field of the Invention

The present invention relates to new compounds and pharmaceutical compositions comprising them, which have inhibition effects on osteoclast differentiation. The pharmaceutical composition comprising new compounds according to the present invention can be used as medicines for treating metabolic bone diseases such as bone metastatic cancer, solid cancer bone metastasis, musculoskeletal complication by solid cancer bone metastasis, hypercalcemia by malignant tumor, multiple myeloma, primary bone tumor, osteoporosis, rheumatoid arthritis, osteoarthritis, periodontal disease, inflammatory resorption of alveolar bone, inflammatory resorption of bone and Paget's disease.

2. Description of the Related Art

Breast cancer is one of the cancers known as the most studies have made compared to all the other cancers. While the studies researched that the breast cancer can be caused by environmental and genetic factors, a certain cause of the cancer has not yet been identified. However, various study results showed possible certain causes of the cancer and there is no controversy that the female hormone estrogen plays an important role in the carcinogenesis of breast cancer. Since breast cells proliferate and differentiate by estrogen stimulations, the risk of breast cancer may be determined by the estrogen exposure period. It means that an increased incidence of breast cancer depends on a longer exposure period to estrogen. In addition, excess intakes of nutrients and fat, genetic factors, obesity, and a hormonal imbalance caused by a long-term administration of contraceptive and female hormone therapy have also been suggested as a possible cause of breast cancer.

The metastasis of cancer often leads to death in cancer patients, especially the breast cancer is recurred by a bone metastasis. According to the clinical cases, it has been reported that the metastasis into the bone tissues was occurred in the 30%-40% of patients who have an early stage transition and in more than 90% of patients who died from the transition. Roughly three causes are considered to induce the bone metastasis. First, a high blood stream mobility following to a lot of blood flow around the red bone marrow of breast cancer cells causes to high access of breast cancer cells to bone tissues. Second, the revelation of surface molecules of orphan cancer cell, i.e., homing receptor of breast cancer cell, and absorbance molecule of bone tissue matrix cells, i.e., drawing ligand molecule may cause it. Finally, existing calcium ($Ca^{2+}$) and growth factor within the bone tissues promote a proliferation of breast cancer cells. When the bone metastasis occurred by a single or a few of breast cancer cells, bone destruction (i.e., bone resorption) may be induced, and the above factors released through the above processes stimulate the proliferation of breast cancer (i.e., vicious cycle) and the majority of patients eventually leads to death.

The bone resorption proceeds by the actions of osteoclasts. The differentiation of osteoclasts may be initiated by the revelation of PTHrP (paratyroid hormone-related protein) and GM-CSF (granulocyte macrophage colony-stimulating factor) molecules which were occurred by the regulated transcription action of activated NF-kappa B (Nuclear Factor-kappa B) in the breast cancer. The PTHrP increases RANKL (RANK ligand) which competes with OPG (osteoprotegrin) in the RANK (receptor activator of NF-kappa B), and concurrently decreases the revelation of OPG (i.e., RANKL antagonist or RANK inhibitor), and thus the PTHrP facilitates the binding of RANK and RANKL. When the RANKL binds to the RANK, the revelation of osteoclast precursors increase. The GM-CSF helps to the generation and differentiation of osteoclast precursors and differentiation of osteoclasts. The NF-kappa B is one of proteins which involved in the cell survival, regulation of immune response, cancer or inflammation, and it has different functions depending on the types of interacting cells and acting point of interaction, like many other transcription factors. NF-kappa B always exists as an active form in the breast cancer cells, and regulates the mechanism of carcinogenesis, proliferation, and metastasis. The activation of NF-kappa B is regulated by IKK (IkB kinase) which phosphorylates IKB (Inhibitor-kB), the activated NF-kappa B is translocated into the nucleus and transcription of target gene initiated.

The only commercially used-medicine for bone disease (bone metastasis of breast cancer and osteoporosis) is zoledronic acid of Novartis. The zoledronic acid is one of bisphosphonates, transformed form of pyrophosphate which used to prevent corrosion of metal pipes etc.

Pharmacokinetically, pyrophosphates having P—O—P can be easily hydrolyzed however, bisphosphonates having P—C—P cannot be easily hydrolyzed and thus it has relatively long-term half-life. Bisphosphonates is used as a treatment for osteoporosis since it reduces bone resorption by inhibiting osteoclasts. $R^1$ among $R^1$ and $R^2$, two lateral chains, binding to carbon atom of bisphosphonates can be binded to calcium of bone by hydroxide (—OH) group, and $R^2$ can be modified in the various forms to increase the inhibition effect of bone resorption. Most of the bisphosphonates are structurally highly hydrophilic and the absorption rate is very low and thus they are formulated to the intravenous injection dosage form. Bisphosphonates attach to the bone surface which the bone formation actively made, and inhibit the maturation of osteoclasts and prevent bone resorption. Also bisphosphonates inhibit the recruitment of osteoclasts to the region of bone resorption and reduce the generation of cytokines to stimulate the bone resorption. Bisphosphonates prevent the invasion of tumor cells and induce the apoptosis of tumor cells in the bone matrix.

Bisphosphonates may have many side effects, such as stroke and atrial fibrillation and the biggest rising problem is known as a bisphosphonates induced osteonecrosis of the jaws (BIONJ), and the exact mechanism of BIONJ is still unknown. BIONJ is a severe bone disease that affects the maxilla, the mandible and the tooth root and the definitive symptom is the exposure of mandibular or maxillary bone. In healthy bone tissue there is a homeostasis between bone resorption and bone apposition. Diseased or damaged bone is resorbed through the osteoclasts mediated process and then osteoblasts form new bone to replace it, thus maintaining healthy bone density. This process is commonly called remodeling.

The main pharmacological action of bisphosphonates is inhibition of the maturation of osteoclast driven bone resorption, and thus bone resorption is inhibited by bisphosphonates, it prevents bone formation by osteoblasts, bone generation is not occurred and thereby micro-damage and fractures are cumulated. Bisphosphonates may affect to the mucous membrane of the gingiva and the tooth root to be exposed outside of the gingiva. Especially in case of frequently masticated jaw bone, the bone turnover rate of jaw is about 10 times higher than the one of normal bone, and thus it is easily affected by bisphosphonates. Also, the bisphosphonates increases the possibility of occurrence of BIONJ by blocking a sufficient blood supply through the inhibition of blood vessels by bisphosphonates.

SUMMARY OF THE INVENTION

The present invention provides method of treating metabolic bone disease, new compounds and pharmaceutical compositions comprising them, which have inhibition effects on osteoclast differentiation and NF-κB transcription.

To solve the above described technical problems, the present invention provides a method of treating metabolic bone disease comprising: single or multiple administration of pharmaceutical composition comprising a compound of the following formula I, or pharmaceutically acceptable salts thereof as an active ingredient to a patient in need thereof,

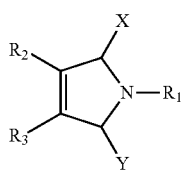

[Formula I]

wherein in Formula I, $R_1$ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring;

$R_2$ and $R_3$ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; and X and Y each independently represent hydrogen, oxo, hydroxy, S or $CH_2$.

The present invention also provides a compound of the following formula I-a or I-b, or pharmaceutically acceptable salts thereof.

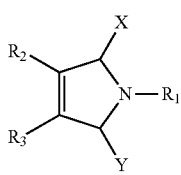

[Formula I-a]

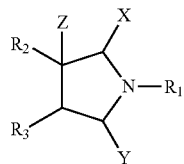

[Formula I-b]

In Formula I-a or I-b, $R_1$ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring. $R_2$ and $R_3$ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring. X and Y each independently represent hydrogen, oxo, hydroxy, S or $CH_2$. Z represents hydrogen, amino$C_{1-6}$alkyl or amino$C_{1-6}$alkyl which is mono-, di- or tri-substituted by $C_{1-6}$alkyl. The above described $C_{6-10}$aryl, $C_{3-10}$cycloalkyl and 5-10 membered heteroaryl including at least one selected from nitrogen atom, oxygen atom and sulfur atom in a ring can be substituted by at least one substituent selected from the groups consisting of halogen, hydroxy, $C_{1-6}$alkyl, halogenated $C_{1-6}$alkyl, alkoxy, amide and carboxy.

The pharmaceutical composition according to the present invention has inhibitory effect on osteoclast differentiation and the inhibitory effect on NF-κB transcription. Thus, they can be used for preventing or treating metabolic bone disease selected from the groups consisting of bone metastatic cancer, solid cancer bone metastasis, musculoskeletal complication by solid cancer bone metastasis, hypercalcemia by malignant tumor, multiple myeloma, primary bone tumor, osteoporosis, rheumatoid arthritis, osteoarthritis, periodontal disease, inflammatory resorption of alveolar bone, inflammatory resorption of bone and Paget's disease.

DESCRIPTION OF THE PREFERRED EMBODIMENTS

Figure 1:
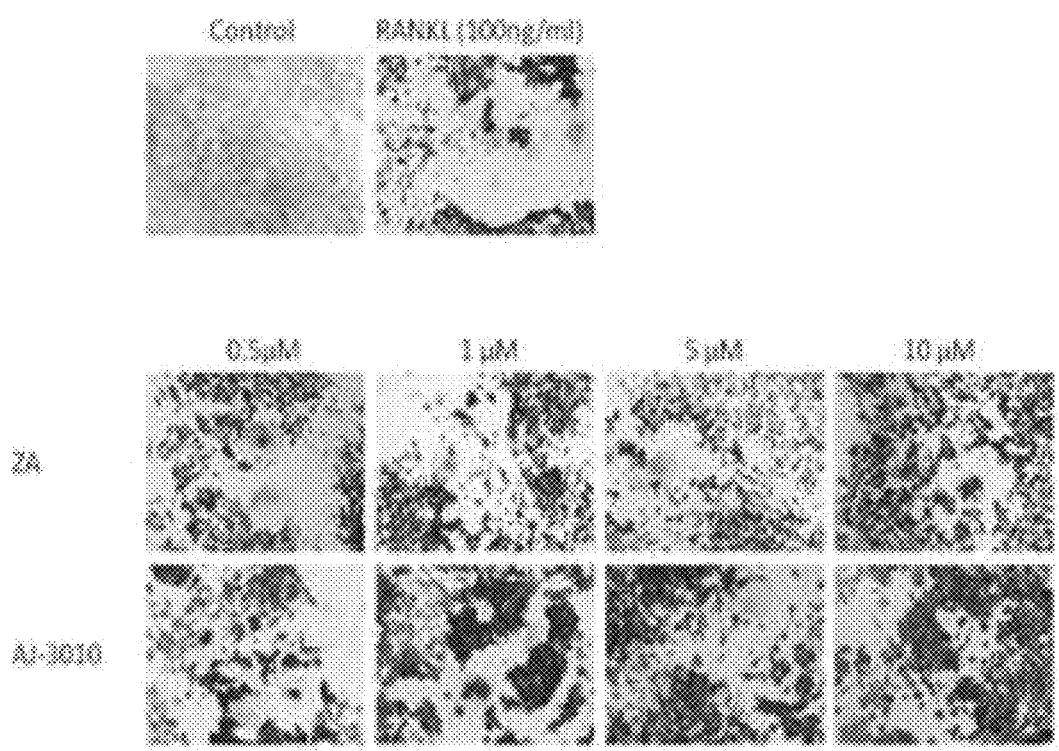
FIG. 1 depicts the dose-dependent inhibitory effect on osteoclast differentiation by treating RAW 264.7 cells with the compound of the invention, zoledronic acid.

The present invention relates to method of treating metabolic bone disease, new compounds and pharmaceutical compositions comprising them, which have inhibition effects on osteoclast differentiation.

The present invention provides a method of treating metabolic bone disease comprising: single or multiple administration of pharmaceutical composition comprising a compound of the following formula I, or pharmaceutically acceptable salts thereof as an active ingredient to a patient in need thereof,

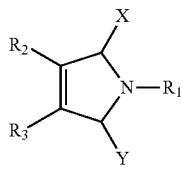
[Formula I]

wherein in Formula I, R₁ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; R₂ and R₃ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; and X and Y each independently represent hydrogen, oxo, hydroxy, S or $CH_2$.

As one aspect of the present invention, in the above described Formula I, R₁ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; R₂ and R₃ each independently represent halogen, phenyl, hydroxy, $C_{6-10}$aryl, $C_{6-10}$aryl$C_{1-6}$alkyl, $C_{3-10}$cycloalkyl or 5-membered heteroaryl including at least one selected from nitrogen atom, oxygen atom and sulfur atom in a ring; and X and Y each independently represent hydrogen, oxo or hydroxyl.

As one aspect of the present invention, the pharmaceutical composition comprising the compound selected from the group consisting of 1-(2,6-diisopropylphenyl)-3,4-diphenyl-1H-pyrrole-2,5-dione; 1,3,4-triphenyl-1H-pyrrole-2,5-dione; 1-(2-chlorophenyl)-3,4-diphenyl-1H-pyrrole-2,5-dione; 1-(3-chlorophenyl)-3,4-diphenyl-1H-pyrrole-2,5-dione; 1-(4-chlorophenyl)-3,4-diphenyl-1H-pyrrole-2,5-dione; 3,4-diphenyl-1-(2-(trifluoromethyl)phenyl)-1H-pyrrole-2,5-dione; 1-cyclohexyl-3,4-diphenyl-1H-pyrrole-2,5-dione; 4-(2,5-dioxo-3,4-diphenyl-2,5-dihydro-1H-pyrrol-1-yl)-2-hydroxybenzoic acid; 5-(2,5-dioxo-3,4-diphenyl-2,5-dihydro-1H-pyrrol-1-yl)-2-hydroxybenzoic acid; 3-chloro-1,4-diphenyl-1H-pyrrole-2,5-dione; 3-chloro-1-(2-chlorophenyl)-4-phenyl-1H-pyrrole-2,5-dione; 3-chloro-1-(3-chlorophenyl)-4-phenyl-1H-pyrrole-2,5-dione; 3-chloro-1-(4-chlorophenyl)-4-phenyl-1H-pyrrole-2,5-dione; 1-(2-fluorophenyl)-3,4-diphenyl-1H-pyrrole-2,5-dione; 1-(3-fluorophenyl)-3,4-diphenyl-1H-pyrrole-2,5-dione; 1-(4-fluorophenyl)-3,4-diphenyl-1H-pyrrole-2,5-dione; 1-benzyl-3,4-diphenyl-1H-pyrrole-2,5-dione; 1-(2-fluorobenzyl)-3,4-diphenyl-1H-pyrrole-2,5-dione; 1-(3-fluorobenzyl)-3,4-diphenyl-1H-pyrrole-2,5-dione; 1-(4-fluorobenzyl)-3,4-diphenyl-1H-pyrrole-2,5-dione; 1-phenethyl-3,4-diphenyl-1H-pyrrole-2,5-dione; 1-(2-fluorophenethyl)-3,4-diphenyl-1H-pyrrole-2,5-dione; 1-(3-fluorophenethyl)-3,4-diphenyl-1H-pyrrole-2,5-dione; 1-(4-fluorophenethyl)-3,4-diphenyl-1H-pyrrole-2,5-dione; 3-(2-chlorophenyl)-1-(4-chlorophenyl)-4-phenyl-1H-pyrrole-2,5-dione; 3-(3-chlorophenyl)-1-(4-chlorophenyl)-4-phenyl-1H-pyrrole-2,5-dione; 1,3-bis(4-chlorophenyl)-4-phenyl-1H-pyrrole-2,5-dione; 1-(4-chlorophenyl)-3-(2,6-dichlorophenyl)-4-phenyl-1H-pyrrole-2,5-dione; 1-(4-chlorophenyl)-5-hydroxy-3,4-diphenyl-1H-pyrrol-2(5H)-one; 1-(4-chlorophenyl)-3,4-diphenyl-1H-pyrrol-2(5H)-one; 1-(4-chlorophenyl)-3-((dimethylamino)methyl)-3,4-diphenylpyrrolidin-2-one; 3-hydroxy-1,4-diphenyl-1H-pyrrole-2,5-dione; 1-(4-chlorophenyl)-3-phenyl-4-(thiophen-2-yl)-1H-pyrrole-2,5-dione; 4-chloro-5-hydroxy-1,3-diphenyl-1H-pyrrol-2(5H)-one; and 1-(4-chlorophenyl)-3,4-diphenyl-2,5-dihydro-1H-pyrrole; or pharmaceutically acceptable salts thereof.

As one aspect of the present invention, the pharmaceutical composition comprising the compound selected from the group consisting of 1-(4-chlorophenyl)-3,4-diphenyl-1H-pyrrole-2,5-dione; 4-(2,5-dioxo-3,4-diphenyl-2,5-dihydro-1H-pyrrol-1-yl)-2-hydroxybenzoic acid; 5-(2,5-dioxo-3,4-diphenyl-2,5-dihydro-1H-pyrrol-1-yl)-2-hydroxybenzoic acid; 3-chloro-1-(2-chlorophenyl)-4-phenyl-1H-pyrrole-2,5-dione; 3-chloro-1-(3-chlorophenyl)-4-phenyl-1H-pyrrole-2,5-dione; 1-(2-fluorophenyl)-3,4-diphenyl-1H-pyrrole-2,5-dione; 1-(3-fluorophenyl)-3,4-diphenyl-1H-pyrrole-2,5-dione; 1-(2-fluorobenzyl)-3,4-diphenyl-1H-pyrrole-2,5-dione; 1-(3-fluorobenzyl)-3,4-diphenyl-1H-pyrrole-2,5-dione; 1-(4-fluorobenzyl)-3,4-diphenyl-1H-pyrrole-2,5-dione; 1-(2-fluorophenethyl)-3,4-diphenyl-1H-pyrrole-2,5-dione; 1-(3-fluorophenethyl)-3,4-diphenyl-1H-pyrrole-2,5-dione; 1-(4-fluorophenethyl)-3,4-diphenyl-1H-pyrrole-2,5-dione; 3-(2-chlorophenyl)-1-(4-chlorophenyl)-4-phenyl-1H-pyrrole-2,5-dione; 3-(3-chlorophenyl)-1-(4-chlorophenyl)-4-phenyl-1H-pyrrole-2,5-dione; 1-(4-chlorophenyl)-3-(2,6-dichlorophenyl)-4-phenyl-1H-pyrrole-2,5-dione; 1-(4-chlorophenyl)-5-hydroxy-3,4-diphenyl-1H-pyrrol-2(5H)-one; 1-(4-chlorophenyl)-3-((dimethylamino)methyl)-3,4-diphenylpyrrolidin-2-one; 1-(4-chlorophenyl)-3-phenyl-4-(thiophen-2-yl)-1H-pyrrole-2,5-dione; and 4-chloro-5-hydroxy-1,3-diphenyl-1H-pyrrol-2(5H)-one, or pharmaceutically acceptable salts thereof.

As one aspect of the present invention, the pharmaceutical composition comprising 1-(4-chlorophenyl)-3,4-diphenyl-1H-pyrrole-2,5-dione as an active ingredient.

As one aspect of the present invention, the metabolic bone disease is selected from the group consisting of bone metastatic cancer, solid cancer bone metastasis, musculoskeletal complication by solid cancer bone metastasis, hypercalcemia by malignant tumor, multiple myeloma, primary bone tumor, osteoporosis, Rheumatoid Arthritis, Osteoarthritis, Periodontal Disease, inflammatory resorption of alveolar bone, inflammatory resorption of bone and Paget's disease.

As one aspect of the present invention, the metabolic bone disease is selected from the group consisting of bone metastatic cancer, solid cancer bone metastasis, musculoskeletal complication by solid cancer bone metastasis, hypercalcemia by malignant tumor and multiple myeloma.

The present invention provides a compound of the following formula I-a or I-b, or pharmaceutically acceptable salts thereof

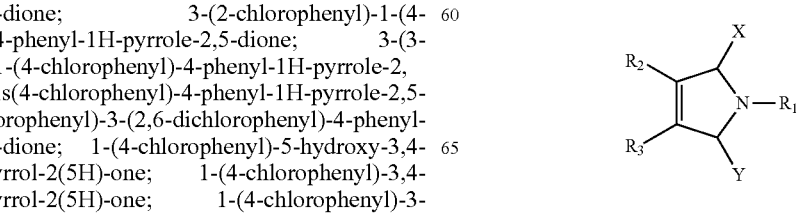
[Formula I-a]

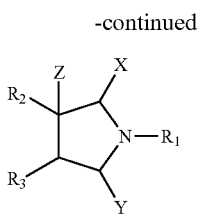

[Formula I-b]

wherein in Formula I-a or I-b, $R_1$ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; $R_2$ and $R_3$ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; X and Y each independently represent hydrogen, oxo, hydroxy, S or $CH_2$; Z represents hydrogen, amino$C_{1-6}$alkyl or amino$C_{1-6}$alkyl which is mono-, di- or tri-substituted by $C_{1-6}$alkyl; and the above $C_{6-10}$aryl, $C_{3-10}$cycloalkyl and 5-10 membered heteroaryl including at least one selected from nitrogen atom, oxygen atom and sulfur atom in a ring can be substituted by at least one substituent selected from the groups consisting of halogen, hydroxy, $C_{1-6}$alkyl, halogenated $C_{1-6}$alkyl, alkoxy, amide and carboxy.

As one aspect of the present invention, in the above described Formula I-a or I-b, $R_1$ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; $R_2$ and $R_3$ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; X and Y each independently represent hydrogen, oxo or hydroxy; Z represents hydrogen or amino$C_{1-6}$alkyl which is mono-, di- or tri-substituted by $C_{1-6}$alkyl; and the above $C_{6-10}$aryl, $C_{3-10}$cycloalkyl and 5-10 membered heteroaryl including at least one selected from nitrogen atom, oxygen atom and sulfur atom in a ring can be substituted by at least one substituent selected from the groups consisting of halogen, hydroxy, $C_{1-3}$alkyl, halogenated $C_{1-3}$alkyl, amide and carboxy.

As another aspect of the present invention, the compound of the above described Formula I-a or I-b can be the compound selected from the groups consisting of
1-(2,6-diisopropylphenyl)-3,4-diphenyl-1H-pyrrole-2,5-dione;
1,3,4-triphenyl-1H-pyrrole-2,5-dione;
1-(2-chlorophenyl)-3,4-diphenyl-1H-pyrrole-2,5-dione;
1-(3-chlorophenyl)-3,4-diphenyl-1H-pyrrole-2,5-dione;
1-(4-chlorophenyl)-3,4-diphenyl-1H-pyrrole-2,5-dione;
3,4-diphenyl-1-(2-(trifluoromethyl)phenyl)-1H-pyrrole-2,5-dione;
1-cyclohexyl-3,4-diphenyl-1H-pyrrole-2,5-dione;
4-(2,5-dioxo-3,4-diphenyl-2,5-dihydro-1H-pyrrol-1-yl)-2-hydroxybenzoic acid;
5-(2,5-dioxo-3,4-diphenyl-2,5-dihydro-1H-pyrrol-1-yl)-2-hydroxybenzoic acid;
3-chloro-1,4-diphenyl-1H-pyrrole-2,5-dione;
3-chloro-1-(2-chlorophenyl)-4-phenyl-1H-pyrrole-2,5-dione;
3-chloro-1-(3-chlorophenyl)-4-phenyl-1H-pyrrole-2,5-dione;
3-chloro-1-(4-chlorophenyl)-4-phenyl-1H-pyrrole-2,5-dione;
1-(2-fluorophenyl)-3,4-diphenyl-1H-pyrrole-2,5-dione;
1-(3-fluorophenyl)-3,4-diphenyl-1H-pyrrole-2,5-dione;
1-(4-fluorophenyl)-3,4-diphenyl-1H-pyrrole-2,5-dione;
1-benzyl-3,4-diphenyl-1H-pyrrole-2,5-dione;
1-(2-fluorobenzyl)-3,4-diphenyl-1H-pyrrole-2,5-dione;
1-(3-fluorobenzyl)-3,4-diphenyl-1H-pyrrole-2,5-dione;
1-(4-fluorobenzyl)-3,4-diphenyl-1H-pyrrole-2,5-dione;
1-phenethyl-3,4-diphenyl-1H-pyrrole-2,5-dione;
1-(2-fluorophenethyl)-3,4-diphenyl-1H-pyrrole-2,5-dione;
1-(3-fluorophenethyl)-3,4-diphenyl-1H-pyrrole-2,5-dione;
1-(4-fluorophenethyl)-3,4-diphenyl-1H-pyrrole-2,5-dione;
3-(2-chlorophenyl)-1-(4-chlorophenyl)-4-phenyl-1H-pyrrole-2,5-dione;
3-(3-chlorophenyl)-1-(4-chlorophenyl)-4-phenyl-1H-pyrrole-2,5-dione;
1,3-bis(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrol-2(5H)-one;
1-(4-chlorophenyl)-3,4-diphenyl-1H-pyrrol-2(5H)-one;
1-(4-chlorophenyl)-3-((dimethylamino)methyl)-3,4-diphenylpyrrolidin-2-one;
3-hydroxy-1,4-diphenyl-1H-pyrrole-2,5-dione;
1-(4-chlorophenyl)-3-phenyl-4-(thiophen-2-yl)-1H-pyrrole-2,5-dione;
4-chloro-5-hydroxy-1,3-diphenyl-1H-pyrrol-2(5H)-one;
1-(4-chlorophenyl)-3,4-diphenyl-2,5-dihydro-1H-pyrrole; and
1-(4-chlorophenyl)-3,4-diphenylpyrrolidine-2,5-dione, or the pharmaceutically acceptable salt thereof.

As another aspect of the present invention, the compound of the above described Formula I-a or I-b can be the compound selected from the groups consisting of
1-(4-chlorophenyl)-3,4-diphenyl-1H-pyrrole-2,5-dione;
4-(2,5-dioxo-3,4-diphenyl-2,5-dihydro-1H-pyrrol-1-yl)-2-hydroxybenzoic acid;
5-(2,5-dioxo-3,4-diphenyl-2,5-dihydro-1H-pyrrol-1-yl)-2-hydroxybenzoic acid;
3-chloro-1-(2-chlorophenyl)-4-phenyl-1H-pyrrole-2,5-dione;
3-chloro-1-(3-chlorophenyl)-4-phenyl-1H-pyrrole-2,5-dione;
1-(2-fluorophenyl)-3,4-diphenyl-1H-pyrrole-2,5-dione;
1-(3-fluorophenyl)-3,4-diphenyl-1H-pyrrole-2,5-dione;
1-(2-fluorobenzyl)-3,4-diphenyl-1H-pyrrole-2,5-dione;
1-(3-fluorobenzyl)-3,4-diphenyl-1H-pyrrole-2,5-dione;
1-(4-fluorobenzyl)-3,4-diphenyl-1H-pyrrole-2,5-dione;
1-(2-fluorophenethyl)-3,4-diphenyl-1H-pyrrole-2,5-dione;
1-(3-fluorophenethyl)-3,4-diphenyl-1H-pyrrole-2,5-dione;
1-(4-fluorophenethyl)-3,4-diphenyl-1H-pyrrole-2,5-dione;
3-(2-chlorophenyl)-1-(4-chlorophenyl)-4-phenyl-1H-pyrrole-2,5-dione;
3-(3-chlorophenyl)-1-(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrol-2(5H)-one;
1-(4-chlorophenyl)-3-((dimethylamino)methyl)-3,4-diphenylpyrrolidin-2-one;
1-(4-chlorophenyl)-3-phenyl-4-(thiophen-2-yl)-1H-pyrrole-2,5-dione;
4-chloro-5-hydroxy-1,3-diphenyl-1H-pyrrol-2(5H)-one; and
1-(4-chlorophenyl)-3,4-diphenylpyrrolidine-2,5-dione, or the pharmaceutically acceptable salt thereof.

As another aspect of the present invention, the compound of the above described Formula I-a or I-b can be the compound selected from the groups consisting of
4-(2,5-dioxo-3,4-diphenyl-2,5-dihydro-1H-pyrrol-1-yl)-2-hydroxybenzoic acid;
5-(2,5-dioxo-3,4-diphenyl-2,5-dihydro-1H-pyrrol-1-yl)-2-hydroxybenzoic acid;
3-chloro-1-(2-chlorophenyl)-4-phenyl-1H-pyrrole-2,5-dione;
3-chloro-1-(3-chlorophenyl)-4-phenyl-1H-pyrrole-2,5-dione;
1-(2-fluorophenyl)-3,4-diphenyl-1H-pyrrole-2,5-dione;
1-(3-fluorophenyl)-3,4-diphenyl-1H-pyrrole-2,5-dione;
1-(2-fluorobenzyl)-3,4-diphenyl-1H-pyrrole-2,5-dione;
1-(3-fluorobenzyl)-3,4-diphenyl-1H-pyrrole-2,5-dione;
1-(4-fluorobenzyl)-3,4-diphenyl-1H-pyrrole-2,5-dione;
1-(2-fluorophenethyl)-3,4-diphenyl-1H-pyrrole-2,5-dione;
1-(3-fluorophenethyl)-3,4-diphenyl-1H-pyrrole-2,5-dione;
1-(4-fluorophenethyl)-3,4-diphenyl-1H-pyrrole-2,5-dione;
3-(2-chlorophenyl)-1-(4-chlorophenyl)-4-phenyl-1H-pyrrole-2,5-dione;
3-(3-chlorophenyl)-1-(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrole-2(5H)-one;
1-(4-chlorophenyl)-3-((dimethylamino)methyl)-3,4-diphenylpyrrolidin-2-one;
1-(4-chlorophenyl)-3-phenyl-4-(thiophen-2-yl)-1H-pyrrole-2,5-dione;
4-chloro-5-hydroxy-1,3-diphenyl-1H-pyrrol-2(5H)-one; and
1-(4-chlorophenyl)-3,4-diphenylpyrrolidine-2,5-dione, or the pharmaceutically acceptable salt thereof.

The present invention provides a pharmaceutical composition for preventing or treating metabolic bone disease comprising a compound of the following formula I-a or I-b, or pharmaceutically acceptable salts thereof as an active ingredient,

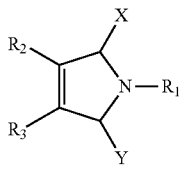

[Formula I-a]

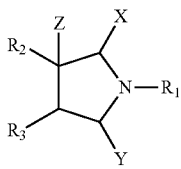

[Formula I-b]

wherein in Formula I-a or I-b, $R_1$ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; $R_2$ and $R_3$ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; X and Y each independently represent hydrogen, oxo, hydroxy, S or $CH_2$; Z represents hydrogen, amino$C_{1-6}$alkyl or amino$C_{1-6}$alkyl which is mono-, di- or tri-substituted by $C_{1-6}$alkyl; and the above $C_{6-10}$aryl, $C_{3-10}$cycloalkyl and 5-10 membered heteroaryl including at least one selected from nitrogen atom, oxygen atom and sulfur atom in a ring can be substituted by at least one substituent selected from the groups consisting of halogen, hydroxy, $C_{1-6}$alkyl, halogenated $C_{1-6}$alkyl, alkoxy, amide and carboxy.

More specifically, in the above described Formula I-a or I-b, $R_1$ represents phenyl, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; $R_2$ and $R_3$ each independently represent halogen, phenyl, hydroxy, $C_{6-10}$aryl, $C_{6-10}$aryl$C_{1-6}$alkyl, $C_{3-10}$cycloalkyl or 5-10 membered heteroaryl including at least one selected from nitrogen atom, oxygen atom and sulfur atom in a ring; X and Y each independently represent hydrogen, oxo or hydroxy; Z represents hydrogen or amino$C_{1-6}$alkyl which is mono-, di- or tri-substituted by $C_{1-6}$alkyl; and the above $C_{6-10}$aryl, $C_{3-10}$cycloalkyl and 5-10 membered heteroaryl including at least one selected from nitrogen atom, oxygen atom and sulfur atom in a ring can be substituted by at least one substituent selected from the groups consisting of halogen, hydroxy, $C_{1-3}$alkyl, halogenated $C_{1-3}$alkyl, amide and carboxy.

The compound of the above Formula I-a or I-b according to the present invention can be the compound selected from the groups consisting of
1-(2,6-diisopropylphenyl)-3,4-diphenyl-1H-pyrrole-2,5-dione;
1,3,4-triphenyl-1H-pyrrole-2,5-dione;
1-(2-chlorophenyl)-3,4-diphenyl-1H-pyrrole-2,5-dione;
1-(3-chlorophenyl)-3,4-diphenyl-1H-pyrrole-2,5-dione;
1-(4-chlorophenyl)-3,4-diphenyl-1H-pyrrole-2,5-dione;
3,4-diphenyl-1-(2-(trifluoromethyl)phenyl)-1H-pyrrole-2,5-dione;
1-cyclohexyl-3,4-diphenyl-1H-pyrrole-2,5-dione;
4-(2,5-dioxo-3,4-diphenyl-2,5-dihydro-1H-pyrrol-1-yl)-2-hydroxybenzoic acid;
5-(2,5-dioxo-3,4-diphenyl-2,5-dihydro-1H-pyrrol-1-yl)-2-hydroxybenzoic acid;
3-chloro-1,4-diphenyl-1H-pyrrole-2,5-dione;
3-chloro-1-(2-chlorophenyl)-4-phenyl-1H-pyrrole-2,5-dione;
3-chloro-1-(3-chlorophenyl)-4-phenyl-1H-pyrrole-2,5-dione;
3-chloro-1-(4-chlorophenyl)-4-phenyl-1H-pyrrole-2,5-dione;
1-(2-fluorophenyl)-3,4-diphenyl-1H-pyrrole-2,5-dione;
1-(3-fluorophenyl)-3,4-diphenyl-1H-pyrrole-2,5-dione;
1-(4-fluorophenyl)-3,4-diphenyl-1H-pyrrole-2,5-dione;
1-benzyl-3,4-diphenyl-1H-pyrrole-2,5-dione;
1-(2-fluorobenzyl)-3,4-diphenyl-1H-pyrrole-2,5-dione;
1-(3-fluorobenzyl)-3,4-diphenyl-1H-pyrrole-2,5-dione;
1-(4-fluorobenzyl)-3,4-diphenyl-1H-pyrrole-2,5-dione;
1-phenethyl-3,4-diphenyl-1H-pyrrole-2,5-dione;
1-(2-fluorophenethyl)-3,4-diphenyl-1H-pyrrole-2,5-dione;
1-(3-fluorophenethyl)-3,4-diphenyl-1H-pyrrole-2,5-dione;
1-(4-fluorophenethyl)-3,4-diphenyl-1H-pyrrole-2,5-dione;
3-(2-chlorophenyl)-1-(4-chlorophenyl)-4-phenyl-1H-pyrrole-2,5-dione;
3-(3-chlorophenyl)-1-(4-chlorophenyl)-4-phenyl-1H-pyrrole-2,5-dione;
1,3-bis(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrol-2(5H)-one;

1-(4-chlorophenyl)-3,4-diphenyl-1H-pyrrol-2(5H)-one;
1-(4-chlorophenyl)-3-((dimethylamino)methyl)-3,4-diphenylpyrrolidin-2-one;
3-hydroxy-1,4-diphenyl-1H-pyrrole-2,5-dione;
1-(4-chlorophenyl)-3-phenyl-4-(thiophen-2-yl)-1H-pyrrole-2,5-dione;
4-chloro-5-hydroxy-1,3-diphenyl-1H-pyrrol-2(5H)-one;
1-(4-chlorophenyl)-3,4-diphenyl-2,5-dihydro-1H-pyrrole; and
1-(4-chlorophenyl)-3,4-diphenylpyrrolidine-2,5-dione, or the pharmaceutically acceptable salt thereof. The present invention provides pharmaceutical composition for preventing or treating metabolic bone disease comprising at least one selected from the above listed compounds or pharmaceutically acceptable salts thereof as an active ingredient.

The compound of the above Formula I-a or I-b according to the present invention can be the compound selected from the groups consisting of
1-(4-chlorophenyl)-3,4-diphenyl-1H-pyrrole-2,5-dione;
4-(2,5-dioxo-3,4-diphenyl-2,5-dihydro-1H-pyrrol-1-yl)-2-hydroxybenzoic acid;
5-(2,5-dioxo-3,4-diphenyl-2,5-dihydro-1H-pyrrol-1-yl)-2-hydroxybenzoic acid;
3-chloro-1-(2-chlorophenyl)-4-phenyl-1H-pyrrole-2,5-dione;
3-chloro-1-(3-chlorophenyl)-4-phenyl-1H-pyrrole-2,5-dione;
1-(2-fluorophenyl)-3,4-diphenyl-1H-pyrrole-2,5-dione;
1-(3-fluorophenyl)-3,4-diphenyl-1H-pyrrole-2,5-dione;
1-(2-fluorobenzyl)-3,4-diphenyl-1H-pyrrole-2,5-dione;
1-(3-fluorobenzyl)-3,4-diphenyl-1H-pyrrole-2,5-dione;
1-(4-fluorobenzyl)-3,4-diphenyl-1H-pyrrole-2,5-dione;
1-(2-fluorophenethyl)-3,4-diphenyl-1H-pyrrole-2,5-dione;
1-(3-fluorophenethyl)-3,4-diphenyl-1H-pyrrole-2,5-dione;
1-(4-fluorophenethyl)-3,4-diphenyl-1H-pyrrole-2,5-dione;
3-(2-chlorophenyl)-1-(4-chlorophenyl)-4-phenyl-1H-pyrrole-2,5-dione;
3-(3-chlorophenyl)-1-(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrol-2(5H)-one;
1-(4-chlorophenyl)-3-((dimethylamino)methyl)-3,4-diphenylpyrrolidin-2-one;
1-(4-chlorophenyl)-3-phenyl-4-(thiophen-2-yl)-1H-pyrrole-2,5-dione;
4-chloro-5-hydroxy-1,3-diphenyl-1H-pyrrol-2(5H)-one; and
1-(4-chlorophenyl)-3,4-diphenylpyrrolidine-2,5-dione, or the pharmaceutically acceptable salt thereof. The present invention provides pharmaceutical composition for preventing or treating metabolic bone disease comprising at least one selected from the above listed compounds or pharmaceutically acceptable salts thereof as an active ingredient.

The present invention provides the pharmaceutical composition for preventing or treating metabolic bone disease comprising 1-(4-chlorophenyl)-3,4-diphenyl-1H-pyrrole-2,5-dione as an active ingredient.

As used herein, the term "alkyl" refers to a straight or branched chain hydrocarbon having from one to five carbon atoms, or from one to seven carbon atoms, or from five to nine carbon atoms, or from six to twelve carbon atoms. Examples of "alkyl" as used herein include, but are not limited to, methyl, ethyl, propyl, n-butyl, n-pentyl, isobutyl, and isopropyl, tert-butyl, and the like.

As used herein the term "aryl" refers to aromatic monocyclic or multicyclic groups containing from 5 to 15 carbon atoms. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment.

As used herein the term "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring.

The term "cycloalkyl" refers to a cyclic ring having from 6 to 12 carbon atoms connected via single bond only.

It is appreciated by a person skilled in the art that certain compounds of the invention may possess at least one stereogenic carbon atom. Thus, it should be noted that the present invention encompasses all possible stereoisomers of such compounds including all possible mixtures thereof, such as for example racemic mixtures, diastereomeric mixtures, non-racemic mixtures etc. It is further noted that compounds of the invention may possess a double bond. Thus, the present invention encompasses any stereoisomer, cis, trans, E or Z stereoisomers of such compounds including any mixture thereof.

The pharmaceutical composition according to the present invention can be used for preventing or treating metabolic bone disease selected from the groups consisting of bone metastatic cancer, solid cancer bone metastasis, musculoskeletal complication by solid cancer bone metastasis, hypercalcemia by malignant tumor, multiple myeloma, primary bone tumor, osteoporosis, rheumatoid arthritis, osteoarthritis, periodontal disease, inflammatory resorption of alveolar bone, inflammatory resorption of bone and Paget's disease.

More specifically, the pharmaceutical composition comprising the compound of Formula I-a or I-b, or the pharmaceutically acceptable salt thereof according to the present invention can be used for preventing or treating metabolic bone diseases selected from the groups consisting of bone metastatic cancer, solid cancer bone metastasis, musculoskeletal complication by solid cancer bone metastasis, hypercalcemia by malignant tumor and multiple myeloma.

When the above mentioned chemical compound is used as pharmaceutically acceptable salt form, the salt can be selected from the allowable salts for treating or preventing bone metabolic diseases among the existing salt forms of active ingredient compounds.

Pharmaceutically acceptable salts of the compounds of this invention include, but are not limited to, acid addition salts those derived from pharmaceutically acceptable free acids. Examples of suitable acid addition salts include inorganic acids such as hydrochloric acid, nitric acid, phosphoric acid, sulfurinc acid, hydrobromic acid, hydroiodic acid, nitrous acid, phosphorous and the like; nontoxic organic acids such as aliphatic mono- and dicarbolxylate, phenyl-substituted alkanoate, hydroxyalkanoate and alkandioate, hetero-acids, aliphatic and hetero sulfonates.

Pharmaceutically nontoxic salts include sulfates, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, iso-butyrate, caprate, heptanoate, propionic oleate, oxalate, malonate, succinate, suberate, sebacate, fumarate, maleate, Butin-1,4-dioate, hexane-1,6-dioate, benzoate, chlorobenzoate, methyl benzoate, dinitro benzoate, hydroxy benzoate, methoxy benzoate, phthalate, terephthalate, benzene sulfonate, toluene sulfonate, chlorobenzene sulfonate, xylene sulfonate, phenyl acetate, phenyl propionate, phenyl butyrate, citrate, lactate, hydroxy butyrate, glycolate, maleate, tartrate, methane sulfonate, propane sulfonate, naphthalene-1-sulfonate, naphthalene-2-sulfonate or mandelate.

The acid addition salts of the invention can be prepared by using conventional methods, for example, the compounds of the invention dissolved in an excess of aqueous acid solution, and the salts are precipitated by using water-miscible organic solvents such as methanol, ethanol, acetone or acetonitrile.

The compounds of the invention can be made as a pharmaceutically acceptable metal salts by using bases. Alkali metal or alkali earth metal salts can be prepared by conventional methods, for example, the compounds are dissolved in an excess of alkali metal hydroxide or alkali earth metal hydroxide solvent, non-soluble compound is filtered, and then the filtrate is obtained by evaporating and drying. Sodium, potassium or calcium salt is preferable as a metal salt. Also, silver salt can be obtained by reacting alkali metal or alkali earth metal salt with suitable silver salt (e.g., silver nitrate).

The pharmaceutical composition of the invention may comprise pharmaceutically acceptable carriers. The pharmaceutical composition of the invention comprising pharmaceutically acceptable carriers may be administered in various oral or non-oral administering formulations. When it is formulated, commonly used diluents and excipients such as fillers, extenders, binders, wetting agents, melting agents, surfactants, and the like are used for the preparation.

As the solid formulations for oral administration, it may be used in the formulations of tablets, pills, capsules (hard/soft), granules, and the like. The solid oral formulations may be prepared by mixing more than one its active ingredient compound(s) with more than one excipient(s) such as starch, calcium carbonate, lactose, and gelatin. In addition to the excipients, lubricants such as stearic acid, magnesium and talc can also be used. As the liquid formulations for oral administration, it may be used in the formulations of suspensions, solutions, emulsions, syrups, and the like. In addition to the commonly used diluents such as water and liquid paraffin, excipients such as wetting agents, sweeteners, fragrances, preservatives, and the like can be used. For non-oral administration, it may be used in the formulations of sterilized solution, non-aqueous solution, suspensions, emulsions, lysophilized formulations, suppository and the like. For the non-aqueous solutions and suspensions, propylene glycol, polyethylene glycol, vegetable oil such as olive oil, and esters such as injection capable ethyloleate can be used. The bases of suppository may include witepsol, macrogol, tween 61, cacao butter, laurin butter, glycerogelatin, and the like. The above stated composition may be sterilized and/or to be sterilized, and contain antiseptic agents, stabilizers, wettable agents or emulsifiers, salts and/or buffers for controlling osmotic pressure, and therapeutically useful agents. The composition may be formulated by traditional methods such as mixing, granulating, or coating.

Pharmaceutically acceptable compositions of this invention may be orally administered in any orally acceptable dosage form including, but not limited to, tablets, pills, powders, granules, capsules, suspensions, aqueous suspensions, solutions, emulsions, syrups, sterilized solution, and the like.

The composition of invention is administered into a patient as a pharmaceutically (therapeutically) effective doasage.

As used herein, "treatment" or "treating," is used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight, gender and age of the subject, the severity of the disease condition, the manner of administration, formulation of the product, health condition, and the like, which can readily be determined by one of ordinary skill in the art. The specific dose will vary depending on the particular compounds chosen, the dosing regimen to be followed, whether it is administered in combination with other compounds, timing of administration, the tissue to which it is administered, and the physical delivery system in which it is carried. In case of standardized to 70 Kg man, general dosage may be 0.1 mg to 1,000 mg/day, preferably 1 to 500 mg/day, more preferably 10 to 100 mg/day and the daily dosage may be administered once or divided over a few times per day at a decision made by a doctor or a pharmacist.

The pharmaceutical composition of the invention may be administered to a patient independently or in a combination therapy with the other therapeutic agents for treating metabolic bone diseases. The composition may be administered to a patient simultaneously or separately with the other therapeutic agents. Also, the composition may be administered in single or multiple. Considering all the above stated factors, it is important to administer adequate dosage to get the maximum effect by the least amount of the compound with minimal side effect and the dosage may be determined easily by those skilled in the art.

The term "co-administration," "administered in combination with," and their grammatical equivalents, as used herein, encompass administration of two or more agents to an animal so that both agents and/or their salts are present in the animal at the same time. Co-administration includes simultaneous administration in separate compositions, administration at different times in separate compositions, or administration in a composition in which both agents are present.

As used herein, the term "subject" (or patient) refers to all animals including humans which have disease or have the possibility to develop the disease to be prevented or treated by inhibiting the differentiation of osteoclast. The above diseases may be effectively prevented or treated by administering the composition comprising the compound of the invention to the subject.

The pharmaceutically acceptable compositions of the invention can be administered to the subject in any conventional administration routes as long as it can be reached to the target tissues. Following to the administering object, the composition of the invention can be administered to the subject in a way of parenteral, intravenous, intramuscular, subcutaneous, intradermal, oral, intranasal, intrapulmonary, and/or intra-rectum administration, but not limited thereto. Also, the above composition can be administered by using any device that can be moved to the target cells.

In one embodiment, the invention may be added to food directly, or used with another food or food ingredients following to the ways of commonly used, but not limited thereto. The amount of the active ingredient may be determined following to the purpose of use (prevention or improvement).

In one embodiment, the invention provides health food functions for preventing or improving metabolic bone disease comprising a compound of the formula I-a or I-b, or its pharmaceutically acceptable salts thereof.

The health food of the invention contains a compound of the formula I-a or I-b, or its pharmaceutically acceptable salts thereof, and further contain proper food supplements.

As used herein, the term, "food supplements" is a component can be added to the various forms of health food and those skilled in the art can be selected and used it properly. The food supplement examples include nutrients, vitamins, minerals (electrolytes), flavors such as synthetic flavors and natural flavors, colorants, fillers, pectic acid and its salts, arginic acid and its salts, organic acid, protective colloidal thickeners, pH adjusters, stabilizer, glycerin, alcohols, carbonates for carbonated beverages, and the like, but is not limited thereto.

In one embodiment, the food composition of the invention may include functional health food. As used herein, the term "functional health food" is the food manufactured or processed with health useful functioning raw materials or ingredients in the forms of tablets, capsules, powders, granules, liquid, pills and the like. As used herein, the term "function" or "functional" refers to functions to obtain the health useful effect for human bodies of adjusting the nutrient and physiological health effects. The functional health food of the invention can be manufactured by commonly used method in the art, and the commonly used raw materials or ingredients can be added to the food. Also, the functional health food has its advantages of no side effect that could happen when drugs are taken for a long term. Since it is also highly portable, the functional health food of the invention can be taken as a supplement for preventing or improving metabolic bone diseases.

The amount of the active ingredient to be added to the food may be determined following to the purpose of its use (prevention or improvement or treatment). Generally, for the food use, the compound of the formula I-a or I-b or its pharmaceutically acceptable salts may be added into the food at the rate of 1-10 wt %, preferably 5 to 10 wt %. However, in case of long-term intakes for improving health and sanitation, or for regulating health conditions, the above stated adding dosage rates can be lowered while the active ingredients has no safety problems.

There are no specific limits in kinds to be the above stated foods. For food examples, it includes commonly understandable health foods such as all kinds of drinks, meat, sausages, breads, biscuits, rice cakes, chocolates, candies, snacks, pizzas, noodles, gums, ice creams, milk products, soups, alcohol/non-alcohol drinks, and vitamin complex, but not limited thereto.

The health food composition can be further comprised of various flavoring agents or natural carbonates as an additive in common food, but is not limited thereto.

The above stated natural carbohydrate examples include monosaccharides, such as glucose, fructose, and etc., disaccharides such as maltose, sucrose and etc., polysaccharides such as commonly used sugars such as dextrin, cyclodextrin, and etc., and alcohol sugars such as xylitol, sorbitol, erythrytol, and etc. As flavoring agents, natural flavoring agents such as taumatin, stevia extract (e.g., levaudioside A, glycyrrhyzine etc.), and synthetic flavoring agents such as saccharine, aspartame, and etc.) may be beneficially added. The above stated natural carbohydrates may be added at the rate of 0.01-0.04 g/100 g of the invented composition, or desirably 0.02-0.03 g/100 g of the invented composition.

The compound according to the present invention can be produced by the following schemes. Aryl or alkyl acetic acid (II) and aryl or alkyl glyoxylic acid were reacted together in acetic anhydride as a preferable solvent with triethylamine as a catalyst for 3-5 hours at 100-120° C. After that, diphenylmaleimide (IV) was synthesized as an intermediate through the purification method using silicagel column chromatography. Diphenylmaleimide intermediate and amine compound were reacted together in toluene as a solvent with triethylamine as a catalyst for 2-5 hours at 120° C. to produce diphenylmaleimide (I).

[Reaction scheme 1]

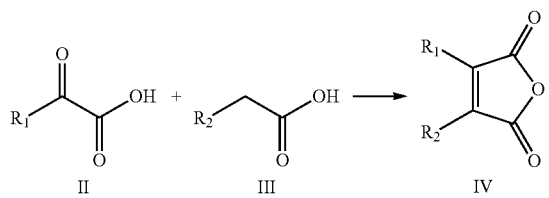

[Reaction scheme 2]

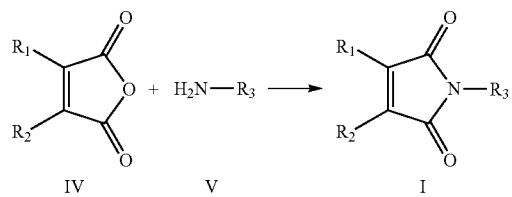

Hereinafter, the present invention can be more specifically described by the following experimental examples and preparation examples. However, they are provided for illustrative purposes only, and the scope of the present invention should not be limited thereto in any manner.

Example 1

The Preparation of Compound 4

[Reaction scheme 3]

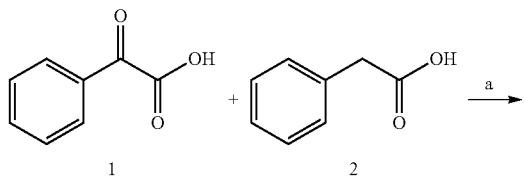

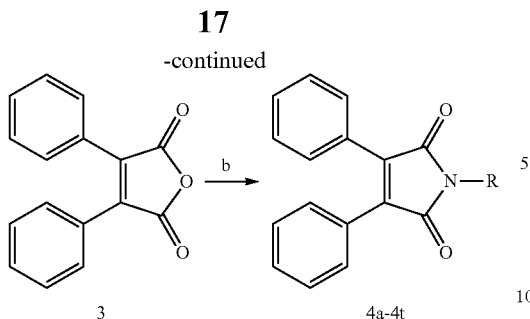

TABLE 1

Substituents of Compound 4

| No | R | No | R |
|---|---|---|---|
| a | 2,6-diisopropylphenyl | b | phenyl |
| c | 2-chlorophenyl | d | 3-chlorophenyl |
| e | 4-chlorophenyl | f | 2-trifluoropentylphenyl |
| g | cyclohexyl | h | 4-carboxy-3-hydroxyphenyl |
| i | 3-carboxy-4-hydroxyphenyl | j | 2-fluorophenyl |
| K | 3-fluorophenyl | l | 4-fluorophenyl |
| m | benzyl | n | 2-fluorobenzyl |
| o | 3-fluorobenzyl | p | 4-fluorobenzyl |
| q | phenethyl | r | 2-fluorophenethyl |
| s | 3-fluorophenethyl | t | 4-fluorophenethyl |

(1) 3,4-diphenylfuran-2,5-dione (3)

After dissolving compound 2 (19.6 g, 96.0 mmol) in acetic anhydride (250 ml), Compound 1 (18.0 g, 80.0 mmol) is added thereto. After 6 hours of reaction with reflux, the temperature was reduced to room temperature, three times extractions were carried out with EA and seven times washings were carried out with brine. Water was removed with anhydrous sodium sulfate and to remove the remaining phenyl acetic acid, the column chromatography was carried out with EA/HX (½). After the distillation under the reduced pressure for the removal of the solvents conducted, vacuum drying was carried out to obtain compound 3.

pale yellow solid (11.0 g, 37.0%); mp 183-184° C.; IR (KBr, cm$^{-1}$) 1756; $^1$H NMR (DMSO$_4$-d$_6$) δ 7.437-7.486 (m, 10H); $^{13}$C NMR (DMSO-d$_6$) δ 127.355, 128.568, 129.243, 130.434, 138.170, 164.873.

(2) Compound 4 (4a-4t)

After dissolving compound 3 (0.50 g, 2.00 mmol) in toluene (10 ml), TEA (0.420 ml, 3.00 mmol) and amine reagents (1.2 equivalents, 2.4 mmol) were added thereto. After 6 hours of the reflux, solvents were removed by the distillation under the reduced pressure. The crystallization was carried out with HX and the column chromatography was carried out with EA/HX (⅛). After the distillation under the reduced pressure for the removal of the solvents, and suspension with HX conducted, vacuum filtration under the reduced pressure and vacuum drying were carried out.

1) 1-(2,6-diisopropylphenyl)-3,4-diphenyl-1H-pyrrole-2,5-dione (4a)

fluorescence pale green solid (0.1 g, 122%); mp 233-234° C.; IR (KBr, cm$^{-1}$) 1713; $^1$H NMR (CDCl$_3$-d) δ 1.199-1.126 (d, 2H), 2.758-2.826 (m, 2H), 7.269-7.288 (d, 2H), 7.367-7.461 (m, 8H), 7.554-7.579 (m, 4H); $^{13}$C NMR (CDCl$_3$-d) δ 24.392, 29.747, 124.038, 127.095, 128.627, 128.687, 129.014, 130.113, 130.174, 136.067, 147.549, 170.453.

2) 1,3,4-triphenyl-1H-pyrrole-2,5-dione (4b)

yellow solid (0.51 g, 39.2%); mp 173-174° C.; IR (KBr, cm$^{-1}$) 1707; $^1$H NMR (CDCl$_3$-d) δ 7.304-7.363 (m, 7H), 7.442-7.454 (m, 4H), 7.503-7.510 (m, 4H); $^{13}$C NMR (CDCl$_3$-d) δ 126.132, 127.732, 128.430, 128.581, 129.036, 129.977, 129.999, 131.736, 136.188, 169.406.

3) 1-(2-chlorophenyl)-3,4-dipheyl-1H-pyrrole-2,5-dione (4c)

pale yellow solid (0.57 g, 40.7%); mp 213-214° C.; IR (KBr, cm$^{-1}$) 1710; $^1$H NMR (CDCl$_3$-d) δ 7.340-7.418 (m, 9H), 7.528-7.563 (m, 5H); $^{13}$C NMR (CDCl$_3$-d) δ 127.777, 128.437, 128.687, 129.728, 130.091, 130.144, 130.477, 130.591, 130.765, 133.276, 136.552, 168.860.

4) 1-(3-chlorophenyl)-3,4-diphenyl-1H-pyrrole-2,5-dione (4d)

dark yellow solid (0.47 g, 33.6%); mp 144-145° C.; IR (KBr, cm$^{-1}$) 1713; $^1$H NMR (CDCl$_3$-d) δ 7.309-7.407 (m, 10H), 7.487-7.511 (m, 4H); $^{13}$C NMR (CDCl$_3$-d) δ 124.092, 126.185, 127.838, 128.255, 128.602, 130.015, 130.166, 132.866, 134.520, 136.332, 169.027.

5) 1-(4-chlorophenyl)-3,4-diphenyl-1H-pyrrole-2,5-dione (4e)

dark yellow solid (0.66 g, 47.1%); mp 198-199° C.; IR (KBr, cm$^{-1}$) 1707: $^1$H NMR (CDCl$_3$-d) δ 7.333-7.402 (m, 7H), 7.410-7.438 (m, 5H), 7.485-7.509 (m, 4H); $^{13}$C NMR (CDCl$_3$-d) 127.247, 128.308, 128.687, 129.264, 130.022, 130.159, 130.326, 133.367, 136.347, 169.194.

6) 3,4-diphenyl-1-(2-(trifluoromethyl)phenyl)-1H-pyrrole-2,5-dione (4f)

fluorescence pale green solid (0.3 g, 19.1%); mp 152-153° C.; IR (KBr, cm$^{-1}$) 1713; $^1$H NMR (CDCl$_3$-d) δ 7.339-7.417 (m, 10H), 7.528-7.562 (m, 4H); $^{13}$C NMR (CDCl$_3$-d) δ 127.777, 128.445, 128.687, 129.734, 130.091, 130.144, 130.477, 130.591, 130.765, 133.283, 136.560, 168.860.

7) 1-cyclohexyl-3,4-diphenyl-1H-pyrrole-2,5-dione (4 g)

fluorescence pale green solid (0.4 g, 303%); mp 159-160° C.; IR (KBr, cm$^{-1}$) 1693; $^1$H NMR (CDCl$_2$-d) δ 1.226-1.410 (m, 3H), 1.670-1.700 (m, 1H), 1.749-1.779 (d, 2H), 1.845, 1.877 (d, 2H), 1.121-2.207 (m, 2H), 4.028-4.089 (m, 1H), 7.327-7.458 (m, 10H); $^{13}$C NMR (CDCl$_3$-d) δ 25.454, 26.326, 30.262, 51.389, 128.521, 128.794, 129.696, 129.954, 135.885, 170.642.

8) 4-(2,5-dioxo-3,4-diphenyl-2,5-dihydro-1H-pyrrol-1-yl)-2-hydroxybenzoic acid (4 h)

yellow solid (0.345 g, 22.4%): mp decomposed; IR (KBr, cm$^{-1}$) 3064, 1710, 1677; $^1$H NMR (DMSO-d$_6$) δ 6.710-6.767 (m, 2H), 7.361-7.462 (m, 10H), 7.782-7.803 (d, 1H); $^{13}$C NMR (DMSO-d$_6$) δ 114.204, 114.500, 119.013, 128.318, 138.455, 129.547, 129.592, 129.534, 134.514, 136.031, 162.689, 168.832, 171.054.

9) 5-(2,5-dioxo-3,4-diphenyl-2,5-dihydro-1H-pyrrol-1-yl)-2-hydroxybenzoic acid (4i)

yellow solid (1.10 g, 71.4%); mp 249-250° C.; IR (KBr, cm$^{-1}$) 3457, 1710, 1587; $^1$H NMR (DMSO-d$_6$) δ 7.096-7.118 (d, 1H), 7.376-7.476 (m, 10H), 7.585-7.613 (m, 1H), 7.908-7.914 (d, 1H); $^{13}$C NMR (DMSO-d$_6$) 113.090, 117.534, 122.979, 128.333, 127.485, 128.834, 129.539, 160.178, 169.128, 170.689.

10) 1-(2-fluorophenyl)-3,4-diphenyl-1H-pyrrole-2,5-dione (4j)

yellow solid (100 mg, 14.6%); mp decomposed: IR (KBr, cm$^{-1}$) 1719, 3471; $^1$H NMR (CDCl$_3$-d) δ 7.223-7.536 (m, 14H); $^{13}$C NMR (CDCl$_3$-d) δ 116.750, 116.947, 119.564, 124.683, 14.721, 128.445, 128.695, 129.871, 130.083, 130.151, 130.568, 130.652, 136.742, 156.650, 159.152, 168.731.

11) 1-(3-fluorophenyl)-3,4-diphenyl-1H-pyrrole-2,5-dione (4k)

yellow solid (324 mg, 46.4%); mp 157-158° C.; IR (KBr, cm$^{-1}$) 1710, 3459; $^1$H NMR (CDCl$_3$-d) δ 7.060-7.523 (m, 14H); $^{13}$C NMR (CDCl$_3$-d) δ 113.451, 113.694, 114.672, 114.877, 121.574, 128.346, 128.748, 130.091, 130.182, 130.235, 130.819, 136.431, 163.839, 169.133.

12) 1-(4-fluorobenzyl)-3,4-diphenyl-1H-pyrrole-2,5-dione (4l)

yellow solid (352 mg, 50.7%); mp 188-189° C.; IR (KBr, cm$^{-1}$) 1710, 3453; $^1$H NMR (CDCl$_3$-d) δ 7.152-7.521 (m, 14H); $^{13}$C NMR (CDCl$_3$-d) δ 116.068, 116.295, 127.770, 128.012, 128.096, 128.430, 128.725, 130.075, 130.174, 136.340, 160.487, 162.944, 169.482.

13) 1-benzyl-3,4-diphenyl-1H-pyrrole-2,5-dione (4m)

pale yellow solid (180 mg, 442%); mp 123-124° C.; IR (KBr, cm$^{-1}$) 1695, 3438; $^1$H NMR (CDCl$_3$-d) δ 4.783 (s, 2H), 7.242-7.461 (m, 15H); $^{13}$C NMR (CDCl$_3$-d) δ 42.230, 127.891, 128.559, 128.604, 128.718, 128.877, 129.863, 129.901, 136.143, 137.446, 170.331.

14) 1-(2-fluorobenzyl)-3,4-diphenyl-1H-pyrrole-2,5-dione (4n)

pale yellow solid (210 mg, 51.6%); mp 113-114° C.; IR (KBr, cm$^{-1}$) 1704, 3444; $^1$H NMR (CDCl$_3$-d) δ 4.895 (s, 2H), 7.031-7.486 (m, 14H); $^{13}$C NMR (CDCl$_3$-d) δ 35.950, 115.597, 115.810, 124.281, 124.312, 128.619, 129.666, 129.742, 129.977, 130.583, 130.621, 1362.34, 170.202.

15) 1-(3-fluorobenzyl)-3,4-diphenyl-1H-pyrrole-2,5-dione (4o)

pale yellow solid (250 mg, 58.3%); mp 107-108° C.; IR (KBr, cm$^{-1}$) 1708, 3438; $^1$H NMR (CDCl$_3$-d) δ 4.788 (s, 2H), 6.956-7.475 (m, 14H); $^{13}$C NMR (CDCl$_3$-d) δ 41.760, 114.900, 115.105, 115.711, 115.924, 124, 418, 128.543, 128.665, 129.954, 130.030, 130.288, 130.371, 136.271, 170.308.

16) 1-(4-fluorobenzyl)-3,4-diphenyl-1H-pyrrole-2,5-dione (4p)

pale yellow solid (271 mg, 65.2%); mp 124-125° C.; IR (KBr, cm$^{-1}$) 1704, 3448; $^1$H NMR (CDCl$_3$-d) 4.759 (s, 2H), 6.981-7.024 (t 2H), 7.302-7.463 (m, 12H); $^{13}$C NMR (CDCl$_3$-d) δ 41.632, 115.537, 115.749, 128.559, 128.619, 129.916, 129.969, 130.765, 130.841, 132.328, 136.211, 161.155, 163.597, 170.346.

17) 1-phenethyl-3,4-diphenyl-1H-pyrrole-2,5-dione (4q)

pale yellow solid (120 mg, 28.3%); mp 164-165° C.; IR (KBr, cm$^{-1}$) 1697, 3444; $^1$H NMR (CDCl$_3$-d) δ 2.978-3.017 (m, 2H), 3.871-3.910 (m, 2H), 7.212-7.448 (m, 15H); $^{13}$C NMR (CDCl$_3$-d) δ 34.964, 39.955, 126.746, 128.627, 128.665, 128.976, 129.886, 129.916, 136.188, 138.130, 170.559.

18) 1-(2-fluorophenethyl)-3,4-diphenyl-1H-pyrrole-2,5-dione (4r)

pale yellow solid (80.0 mg, 10.8%); mp 111-112° C.; IR (KBr, cm$^{-1}$) 1697, 3442; 1H NMR (CDCl$_3$-d) δ 3.026-3.062 (t, 2H) 3.901-3.937 (t, 2H): 7.001-7.435 (m, 14H); $^{13}$C NMR (CDCl$_3$-d) δ 28.556, 38.529, 115.385, 115.605, 124.198, 124.198, 124.236, 125.100, 128.604, 128.680, 129.855, 129.893, 129.984, 131.145, 131.198, 136.165, 162.641, 170.445.

19) 1-(3-fluorophenethyl)-3,4-diphenyl-1H-pyrrole-2,5-dione (4s)

pale yellow solid (35.0 mg, 7.8%); mp 129-130° C.; IR (KBr, cm$^{-1}$) 1702, 3448; $^1$H NMR (CDCl$_3$-d) δ 2.978-3.016 (t, 2H), 3.868-3.906 (m, 2H), 6.906-7.051 (m, 2H), 7.242-7.450 (m, 12H); $^{13}$C NMR (CDCl$_3$-d) δ 34.684, 39.629, 113.633, 113.846, 115.817, 116.030, 124.607, 128.665, 129.916, 129.954, 130.098, 130.182, 136.234, 170.506.

20) 1-(4-fluorophenethyl)-3,4-diphenyl-1H-pyrrole-2,5-dione (4t)

pale yellow solid (32.0 mg, 72%); mp 153-154° C.; IR (KBr, cm$^{-1}$) 1700, 3446; $^1$H NMR (CDCl$_3$-d) δ 2.953-2.992 (t, 2H), 3.847-3.885 (m, 2H), 6.971-7.014 (m, 2H), 7.202-7.451 (m, 12H); $^{13}$C NMR (CDCl$_3$-d) δ 34.130, 39.917, 115.415, 115.628, 128.665, 129.909, 129.954, 130.379, 130.462, 136.188, 162.967, 170.551.

Example 2

The Preparation of Compounds 5, 6 and 7

[Reaction scheme 4]

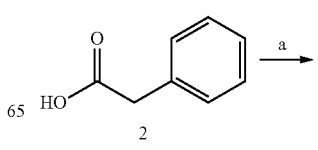

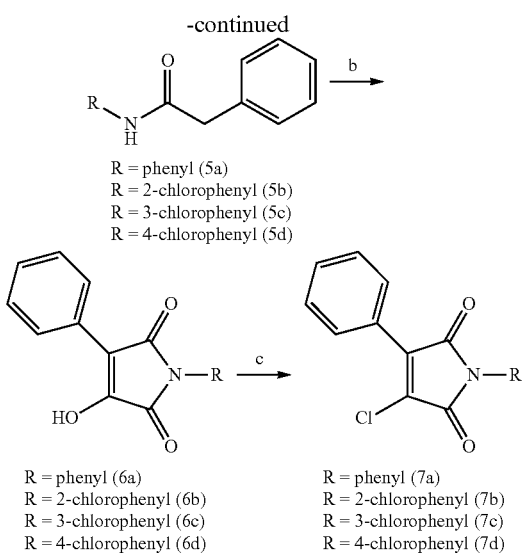

-continued

R = phenyl (5a)
R = 2-chlorophenyl (5b)
R = 3-chlorophenyl (5c)
R = 4-chlorophenyl (5d)

R = phenyl (6a)
R = 2-chlorophenyl (6b)
R = 3-chlorophenyl (6c)
R = 4-chlorophenyl (6d)

R = phenyl (7a)
R = 2-chlorophenyl (7b)
R = 3-chlorophenyl (7c)
R = 4-chlorophenyl (7d)

(1) The synthesis of N,2-diphenylacetamide (5a)

After dissolving compound 2 (1.00 g, 7.34 mmol) in MC (30 ml), the activation for 30 minutes was carried out by the addition of DCC (1.82 g, 8.81 mmol). After the sufficient activation, aniline (0.75 g, 8.07 mmol) was added thereto and the agitation for 6 hours was carried out at room temperature. After the identification of the reaction progress with TLC, DCU was removed by the filtration and solvents were removed by the distillation under the reduced pressure. Then, the next reaction was followed without the purification process.

(2) The synthesis of N-(2-chlorophenyl)-2-phenylacetamide (5b)

After dissolving compound 2 (5.00 g, 36.7 mmol) in MC (50 ml), the activation for 30 minutes was carried out by the addition of DCC (9.10 g, 44.5 mmol). After the sufficient activation, 2-chloroaniline (5.15 g, 40.4 mmol) was added thereto and the agitation for 6 hours was carried out at room temperature. After the identification of the reaction progress with TLC, DCU was removed by the filtration and solvents were removed by the distillation under the reduced pressure. Then, the next reaction was followed without the purification process.

(3) The synthesis of N-(3-chlorophenyl)-2-phenylacetamide (5c)

After dissolving compound 2 (1.00 g, 7.34 mmol) in MC (30 ml), the activation for 30 minutes was carried out by the addition of DCC (1.82 g, 8.81 mmol). After the sufficient activation, 3-chloroaniline (1.03 g, 8.07 mmol) was added thereto and the agitation for 6 hours was carried out at room temperature. After the identification of the reaction progress with TLC, DCU was removed by the filtration and solvents were removed by the distillation under the reduced pressure. Then, the next reaction was followed without the purification process.

(4) The synthesis of N-(4-chlorophenyl)-2-phenylacetamide (5d)

After dissolving compound 2 (1.00 g, 7.34 mmol) in DCM (30 ml), the activation for 30 minutes was carried out by the addition of DCC (1.82 g, 8.81 mmol). After the sufficient activation, 4-chloroaniline (1.03 g, 8.07 mmol) was added thereto and the agitation for 6 hours was carried out at room temperature. After the identification of the reaction progress with TLC, DCU was removed by the filtration and solvents were removed by the distillation under the reduced pressure. Then, the next reaction was followed without the purification process.

(5) The synthesis of 3-hydroxy-1,4-diphenyl-1H-pyrrole-2,5-dione (6a)

After the addition of anhydride THF (20 ml) to compound 5a (1.55 g, 7.34 mmol), the temperature was adjusted to 0° C. Diethyloxalate (1.45 g, 9.50 mmol) and potassium t-butoxide (1.35 g, 11.9 mmol) were added thereto and the agitation for 3 hours was carried out. After the identification of the reaction progress with TLC, the solution was poured into the distilled water and acidified with 1N HCL aqueous solution. Three times extractions were carried out with EA and three times washings were carried out with brine. Water was removed by using $Na_2SO_4$, solvents were removed and then, the suspension was carried out by HX.

(6) The synthesis of 1-(2-chlorophenyl)-3-hydroxy-4-phenyl-1H-pyrrole-2,5-dione (6b)

After the addition of anhydride THF (20 ml) to compound 5b (1.40 g, 7.34 mmol), the temperature was adjusted to 0° C. Diethyloxalate (1.45 g, 9.50 mmol) and potassium t-butoxide (1.35 g, 11.9 mmol) were added thereto and the agitation for 3 hours was carried out. After the identification of the reaction progress with TLC, the solution was poured into the distilled water and acidified with 1N HCL aqueous solution. Three times extractions were carried out with EA and three times washings were carried out with brine. Water was removed by using $Na_2SO_4$, solvents were removed and then, crude purification was carried out by the column chromatography (EA/HX, 1/5).

(7) The synthesis of 1-(3-chlorophenyl)-3-hydroxy-4-phenyl-1H-pyrrole-2,5-dione (6c)

After the addition of anhydride THF (20 ml) to compound 5c (1.55 g, 7.34 mmol), the temperature was adjusted to 0° C. Diethyloxalate (1.45 g, 9.50 mmol) and potassium t-butoxide (1.35 g, 11.9 mmol) were added thereto and the agitation for 3 hours was carried out. After the identification of the reaction progress with TLC, the solution was poured into the distilled water and acidified with 1N HCL aqueous solution. Three times extractions were carried out with EA and three times washings were carried out with brine. Water was removed by using $Na_2SO_4$, solvents were removed and then, the suspension was carried out by EA/HX (1/3).

(8) The synthesis of 1-(4-chlorophenyl)-3-hydroxy-4-phenyl-1H-pyrrole-2,5-dione (6d)

After the addition of anhydride THF (20 ml) to compound 5d (1.40 g, 7.34 mmol), the temperature was adjusted to 0° C. Diethyloxalate (1.45 g, 9.50 mmol) and potassium t-butoxide (1.35 g, 11.9 mmol) were added thereto and the agitation for 3 hours was carried out. After the identification of the reaction progress with TLC, the solution was poured into the distilled water and acidified with 1N HCL aqueous solution. Three times extractions were carried out with EA and three times washings were carried out with brine. Water was removed by using Na₂SO₄ and solvents were removed. Crude purification was carried out by the column chromatography but the next reaction was followed since the purified compound was small in quantity.

(9) The synthesis of 3-chloro-1,4-diphenyl-1H-pyrrole-2,5-dione (7a)

After dissolving compound 6a (2.00 g, 7.54 mmol) in MC (10 ml) and anhydrous DMF (10 ml), oxalyl chloride (1.90 g, 15.0 mmoL) was added thereto and the agitation for 30 minutes was carried out. After the identification of the reaction progress with TLC, the reaction was terminated. Then, three times extractions were carried out with EA and three times washings were carried out with brine. Water was removed by using Na₂SO₄, solvents were removed and then, the column chromatography was carried out with EA/HX (1/9). As the result, Compound 7a was obtained.

pale yellow solid (121 g, 56.1%); mp 82-83° C.; IR (KBr, cm⁻¹) 1782, 1724; ¹H NMR (CDCl₃-d) δ 7.316-7.492 (m, 8H), 7.921-7.946 (m, 2H); ¹³C NMR (CDCl₃-d) δ 126.025, 126.822, 128.103, 128.619, 129.097, 129.704, 130.940, 131.054, 131.372, 134.853, 163.976, 167.025.

(10) The synthesis of 3-chloro-1-(2-chlorophenyl)-4-phenyl-1H-pyrrole-2,5-dione (7b)

After dissolving compound 6b (3.00 g, 10.0 mmol) in MC (10 ml) and anhydrous DMF (10 ml), oxalyl chloride (2.50 g, 20.0 mmoL) was added thereto and the agitation for 30 minutes was carried out. After the identification of the reaction progress with TLC, the reaction was terminated. Then, three times extractions were carried out with EA and three times washings were carried out with brine. Water was removed by using anhydrous Na₂SO₄, solvents were removed and then, the column chromatography was carried out with EA/HX (1/15). The suspension was carried out with HX to obtain compound 7b.

white solid (0.500 g, 15.7%); mp 132-133° C.; IR (KBr, cm⁻¹) 1787, 1739; ¹H NMR (CDCl₃-d) δ 7.286-7.392 (m, 3H), 7.459-7.514 (m, 4H) 7.963-7.987 (m, 2H); ¹³C NMR (CDCl₃-d) δ 126.739, 127.755, 128.642, 128.764, 129.704, 130.349, 130.561, 130.887, 131.062, 131.342, 133.003, 135.400, 163.400, 166.388.

(11) The synthesis of 3-chloro-1-(3-chlorophenyl)-4-phenyl-1H-pyrrole-2,5-dione (7c)

After dissolving compound 6c (2.00 g, 6.67 mmol) in DCM (10 ml) and anhydrous DMF (10 ml), oxalyl chloride (1.69 g, 13.3 mmoL) was added thereto and the agitation for 30 minutes was carried out. After the identification of the reaction progress with TLC, the reaction was terminated. Then, three times extractions were carried out with EA and three times washings were carried out with brine. Water was removed by using Na₂SO₄, solvents were removed and then, the column chromatography was carried out with EA/HX (1/9). The suspension was carried out with EA/HX (1/3) to obtain compound 7c.

yellow solid (1.02 g, 48.2%); mp 67-68° C.; IR (KBr, cm⁻¹) 1778, 1722; ¹H NMR (CDCl₃-d) δ 7.289-7.494 (m, 7H), 7.924-7.949 (m, 2H); ¹³C NMR (CDCl₃-d) δ 124.023, 126.094, 126.678, 128.286, 128.741, 129.757, 130.113, 131.183, 131.509, 132.161, 134.633, 135.081, 163.665, 166.691.

(12) The synthesis of 3-chloro-1-(4-chlorophenyl)-4-phenyl-1H-pyrrole-2,5-dione (7d)

After dissolving compound 6d (1.00 g, 3.33 mmol) in MC (10 ml) and anhydrous DMF (10 ml), oxalyl chloride (0.850 g, 6.66 mmoL) was added thereto and the agitation for 30 minutes was carried out. After the identification of the reaction progress with TLC, the reaction was terminated. Then, three times extractions were carried out with EA and three times washings were carried out with brine. Water was removed by using Na₂SO₄, solvents were removed and then, the column chromatography was carried out with EA/HX (1/15). The suspension was carried out with HX to obtain compound 7d.

yellow solid (0.610 g, 55.5%); mp 116-117° C.; IR (KBr, cm⁻¹) 1780, 1727; ¹H NMR (CDCl₃-d) δ 7.320-7.508 (m, 7H), 7.921-7.945 (m, 2H); ¹³C NMR (CDCl₃-d) δ 126.686, 127.148, 128.726, 129.348, 129.568, 129.727, 131.145, 131.471, 133.830, 135.066, 163.802, 166.836.

Example 3

The Preparation of Compound 8

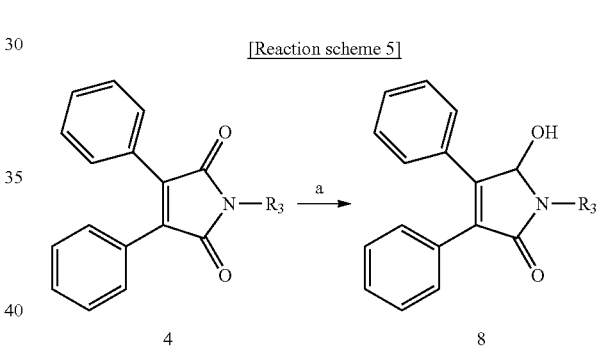

[Reaction scheme 5]

The synthesis of 5-hydroxy-1,3,4-triphenyl-1H-pyrrol-2(5H)-one (8)

After the addition of compound 4e (1.00 g, 2.78 mmol) in methanol, NaBH₄ was slowly added thereto in acetone-ice bath and the agitation for 3 hours was carried out at room temperature. After the identification of disappearance of compound 4e with TLC, quenching was carried out with in HCL aqueous solution in the ice bath. Then, three times extractions were carried out with EA and three times washings were carried out with brine. Water was removed by using Na₂SO₄, solvents were removed and then, the column chromatography was carried out with EA/HX (1/4). After the distillation under the reduced pressure, vacuum drying was carried out to obtain compound 8 white solid (0.71 g, 70.9%); mp 186-187° C.; IR (KBr, cm⁻¹) 3326, 1672; ¹H NMR (CDCl₃-d) δ 6.325-6.503 (m, 1H), 7.279-7.476 (m, 12H), 7.847-7.869 (m, 2H); ¹³C NMR (CDCl₃-d) δ 82.205, 121.498, 127.793, 127.884, 128.043, 128.187, 128.475, 128.521, 128.771, 129.120, 130.371, 131.152, 131.387, 131.801, 149.536, 167.244.

Example 4

The Preparations of Compounds 11, 12, 13 and 14

[Reaction scheme 6]

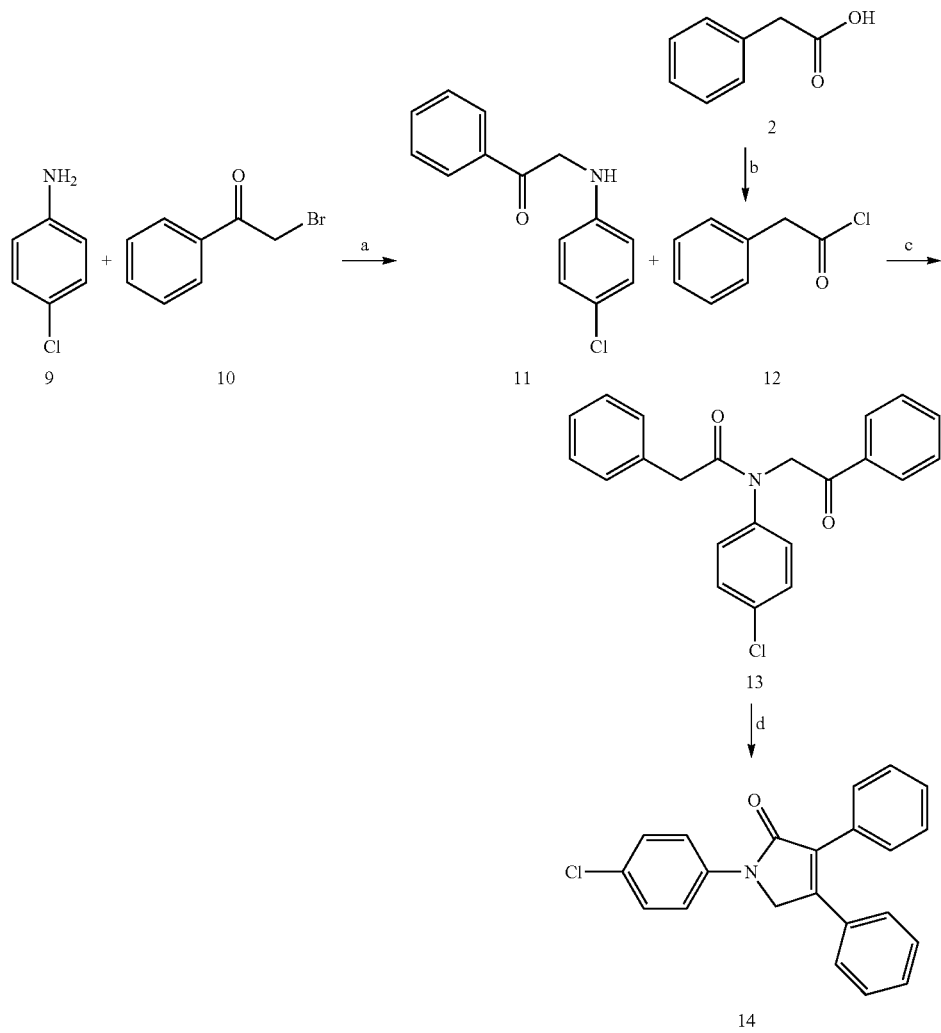

(1) The synthesis of 2-((4-chlorophenyl)amino)-1-phenylethanone (11)

After the addition of compound 9 (2.00 g, 10.2 mmol) in ethanol, NaHCO$_3$ (854 mg, 10.2 mmol) was added thereto. After the activation for 30 minutes at room temperature, compound 10 (1.30 g, 10.2 mmol) was added thereto and the agitation for 3 hours was carried out. After the identification of the reaction progress with TLC, three times extractions were carried out with EA and three times washings were carried out with brine. Water was removed by using Na$_2$SO$_4$ and distillation under the reduced pressure and vacuum drying were carried out. Then, the next reaction was followed without the purification process.

(2) The synthesis of 2-phenylacetyl chloride (12)

After dissolving compound 2 (2.00 g, 14.7 mmol) in SOCl$_2$ (30 ml), the droppings were carried out at 0° C. After the agitation for 1 hour at room temperature, solvents were removed by the distillation under the reduced pressure. Then, the next reaction was followed without the purification process.

(3) The synthesis of N-(4-chlorophenyl)-N-(2-oxo-2-phenylethyl)-2-phenylacetamide (13)

After dissolving compound 12 (2.27 g, 14.7 mmol) in THF, compound 11 (1.5 g, 6.1 mmol) was added thereto. After the agitation for 2 hours at room temperature, three times extractions were carried out with EA and three times washings were carried out with brine. Water was removed by using Na$_2$SO$_4$ and distillation under the reduced pressure was carried out. After the removal of a junk by column chromatography (EA/HX=1/9), the next reaction was followed as a crude condition.

(4) The synthesis of 1-(4-chlorophenyl)-3,4-diphenyl-1H-pyrrol-2(5H)-one (14)

After dissolving compound 13 (2.22 g, 6.1 mmol) in ethanol/H$_2$O (v/v=1/1) 40 ml, K$_2$CO$_3$ (1.70 g, 12.2 mmol) was added thereto and the activation was carried out at room temperature. After the activation, the reflux was conducted.

After the identification of the reaction termination with TLC, the solution was dropped in the distilled water. After the produced solid was distilled under the reduced pressure, the washing was conducted by diethyl ether.

white solid (1.57 g, 71.6%); mp 173° C.; IR (KBr, cm$^{-1}$) 1673; $^1$H NMR (CDCl$_3$-d) δ 4.568 (s, 2H), 7.212-8.399 (m, 12H), 7.728-7.757 (m, 2H); $^{13}$C NMR (CDCl$_3$-d) δ 52.436, 119.556, 127.641, 128.323, 128.430, 128.741, 128.778, 129.006, 129.522, 129.590, 131.281, 132.320, 132.972, 137.864, 147.056, 169.285.

Example 5

The Preparations of Compounds 16 and 17

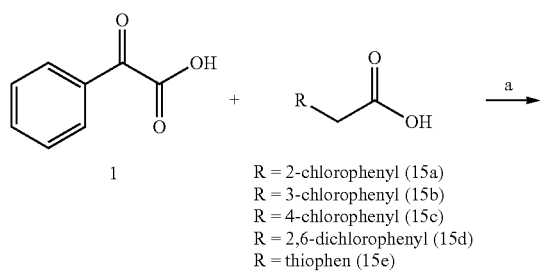

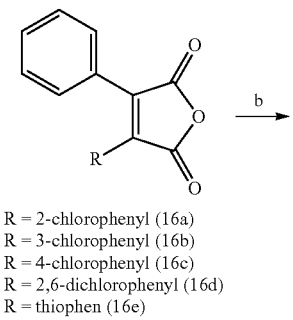

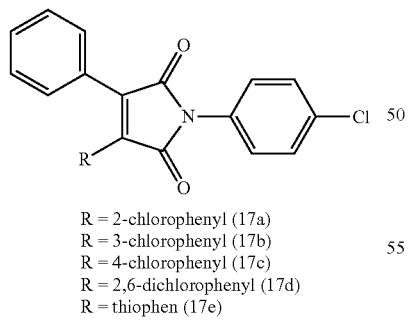

(1) The Synthesis of Compound 16 (16a-16e)

After melting compound 1 (1.00 g, 7.11 mmol) in acetic anhydride (30 ml), compound 15 (6.51 mmol) and TEA (1 ml) were sequentially added thereto. After 6 hours of the reaction with the reflux, the temperature was reduced to room temperature. Three times extractions were carried out with EA and seven times washings were carried out with brine. Water was removed by using Na$_2$SO$_4$ and distillation under the reduced pressure was carried out. Then, the next reaction was followed without the purification process.

(2) The Synthesis of Compound 17 (17a-17e)

After melting compound 16 (4.00 mmol) in toluene (5 ml), TEA (0.840 ml, 6.00 mmol) and 4-chloroaniline (600 mg, 4.80 mmol) were added thereto. After the reflux for 6 hours, Three times extractions were carried out with EA and five times washings were carried out with distilled water and brine, respectively. Water was removed by using Na$_2$SO$_4$ and column chromatography was carried out with EA/HX (⅕).

(3) The synthesis of 3-(2-chlorophenyl)-1-(4-chlorophenyl)-4-phenyl-1H-pyrrol-2,5-dione (17a)

pale yellow solid (700 mg, 26%); mp 46° C.; IR (KBr, cm$^{-1}$) 1716; $^1$H NMR (CDCl$_3$-d) δ 7.287-7.494 (m, 13H); $^{13}$C NMR (CDCl$_3$-d) δ 126.979, 128.154, 128.192, 128.412, 129.034, 129.481, 130.027, 130.353, 130.831, 130.922, 133.182, 133.486, 135.177, 138.605, 167.925, 168.584.

(4) The synthesis of 3-(3-chlorophenyl)-1-(4-chlorophenyl)-4-phenyl-1H-pyrrol-2,5-dione (17b)

pale yellow solid (300 mg, 11.4%); mp 51° C.; IR (KBr, cm$^{-1}$) 1712; $^1$H NMR (CDCl$_3$-d) δ 7.215-7.508 (m, 13H); $^{13}$C NMR (CDCl$_3$-d) δ 126.872, 127.517, 127.835, 128.511, 128.973, 129.587, 129.606, 129.762, 129.883, 130.240, 133.144, 134.305, 134.418, 137.020, 168.440, 168.509.

(5) The synthesis of 3-(4-chlorophenyl)-1-(4-chlorophenyl)-4-phenyl-1H-pyrrol-2,5-dione (17c)

pale yellow solid (1.01 g, 38.1%); mp 157° C.; IR (KBr, cm$^{-1}$) 1710; $^1$H NMR (CDCl$_3$-d) 7.290-7.476 (m, 13H); $^{13}$C NMR (CDCl$_3$d) δ 126.470, 126.903, 127.775, 128.541, 128.761, 128.988, 129.656, 129.929, 130.096, 131.104, 133.152, 134.752, 136.079, 126.352, 168.622.

(6) The synthesis of 1-(4-chlorophenyl)-3-(2,6-dichlorophenyl)-4-phenyl-1H-pyrrol-2,5-dione (17d)

pale yellow solid (200 mg, 7.6%); mp 134° C.; IR (KBr, cm$^{-1}$) 1718; $^1$H NMR (CDCl$_3$-d) 7.326-7.529 (m, 12H); $^{13}$C NMR (CDCl$_3$-d) δ 127.032, 127.919, 128.169, 128.594, 129.041, 129.102, 129.982, 130.748, 131.233, 133.334, 133.364, 134.889, 140.99, 168.372.

(7) The synthesis of 1-(4-chlorophenyl)-3-phenyl-4-(thiophen-2-yl)-1H-pyrrol-2,5-dione (17e)

Orange solid (1.24 g, 67.0%); mp 176-177° C.; IR (KBr, cm$^{-1}$) 1704; $^1$H NMR (DMSO-d$_6$) δ 7.092-7.114 (t, 1H), 7.467-7.549 (m, 9H), 7.687-7.763 (m, 2H); $^{13}$C NMR (CDCl$_3$-d) δ 127.856, 128.538, 128.842, 128.978, 129.183, 129.608, 129.942, 129.987, 130.526, 130.928, 131.929, 132.391, 132.543, 168.639, 159.064.

Example 6

The Preparations of Compounds 18, 19, 20 and 21

[Reaction scheme 6]

(1) The synthesis of 3,4-diphenylfuran-2(5H)-one (18)

After dissolving compound 2 (5.00 g, 36.7 mmol) in ACN (30 ml), compound 10 (7.31 g, 36.7 mmol) and TEA (5.63 ml) were sequentially added thereto. After the agitation for 30 minutes at room temperature, the temperature was reduced to 0° C., DBU (16.5 ml) was dropped and the agitation for 1 hour was carried out. After the termination of the reaction, EA and 1N HCL aqueous solution were added thereto and the organic layer was washed three times with brine. Water was removed by using anhydrous $Na_2SO_4$ and the distillation under the reduced pressure was carried out to obtain compound 18.

Pale yellow solid (7.12 g, 82.1%); mp 113° C.; $^1$H NMR ($CDCl_3$) δ 5.120 (s, 2H), 7.288-7.420 (m, 1H); $^{13}$C NMR (DMSO-$d_6$) δ 70.394, 125.605, 127.159, 128.312, 128.410, 128.630, 128.896, 129.851, 130.246, 130.390, 155.913, 173.024.

(2) The synthesis of (Z)-2,3-diphenylbut-2-ene-1,4-diol (19)

After dissolving compound 18 (1.00 g, 4.23 mmol) in THF (20 ml), the temperature was reduced to or and DIBAL-H (12.96 ml) was dropped. After the agitation for 3 hours was carried out, the reaction was terminated and the extraction was conducted with EA. The organic layer was washed five times with brine and the column chromatography was carried out to obtain compound 19.

White solid (512 mg, 50.7%) mp 79° C.; $^1$H NMR ($CDCl_3$) δ 2.930 (s, 2H), 4.599 (s, 4H), 7.026-7.129 (nm, 10H); $^{13}$C NMR (DMSO-$d_6$) δ 64.151, 126.491, 127.758, 128.205, 128.342, 128.357, 129.108, 140.713, 140.956.

(3) The synthesis of (Z)-(1,4-dibromobut-2-ene-2,3-diyl)dibenzene (20)

After dissolving compound 19 (300 mg, 1.25 mmol) in THF (10 ml), PBr3 (338 mg, 1.25 mmol) was dropped at 0° C. After the agitation for 10 minutes at room temperature, the reflux was conducted for 3 hours. After the termination of the reaction, the temperature was reduced to room temperature. EA and water were added thereto and the organic layer was washed three times with brine. Water was removed by using anhydrous $Na_2SO_4$ and the distillation under the reduced pressure was carried out for the removal of the solvent. Then, column chromatography was conducted to obtain compound 20.

White solid (320 mg, 70.0%); mp 98° C.; $^1$H NMR ($CDCl_3$) 4.511 (s, 4H), 7.057-7.081 (m, 4H), 7.131-7.148 (m, 6H): $^{13}$C NMR ($CDCl_3$) δ 35.101, 126.403, 127.921, 128.643, 131.241, 139.402.

(4) The synthesis of 1-(4-chlorophenyl)-3,4-diphenyl-2,5-dihydro-1H-pyrrole (21)

After dissolving compound 20 (300 mg, 0.819 mmol) and 4-chloroaniline (105 mg, 0.819 mmol) in DCM (10 ml), TEA (457 l, 3.28 mmol) was added thereto and the reflux was conducted for 4 hours. After the termination of the reaction, the temperature was reduced to room temperature and water was added thereto. The organic layer was washed with water and water was removed by using anhydrous Na₂SO₄. After the distillation under the reduced pressure was carried out for the removal of the solvent, column chromatography was conducted to obtain compound 21.

Pale yellow solid (80 mg, 30.0%); mp 158° C.; ¹H NMR (CDCl₃) δ 4.291 (s, 4H), 6.370-6.392 (d, 2H), 6.892-7.188 (m, 12H); ¹³C NMR (CDCl₃) δ 66.410, 115.703, 127.231, 127.405, 127.928, 128.642, 129.302, 140.684, 144.988.

Example 7

The Preparation of Compound 23

[Reaction scheme 7]

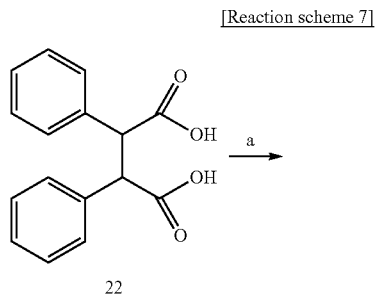

22

The synthesis of 1-(4-chlorophenyl)-3,4-diphenylpyrrolidine-2,5-dione (23)

After dissolving compound 22 (200 mg, 0.740 mmol) in DCM (10 ml), EDC (284 mg, 1.48 mmol) and HOBt (200 mg, 1.48 mmol) were added thereto and the agitation for 24 hours was conducted at room temperature. After the termination of the reaction, the distillation under the reduced pressure was carried out. The produced solid was removed and compound 23 was obtained by the column chromatography.

White solid (50 mg, 11.2%); mp 176° C.; ¹H NMR (CDCl₃) δ 4.226 (s, 4H), 7.241-7.265 (m, 4H), 7.349-7.416 (m, 8H), 7.444-7.466 (d, 2H); ¹³C NMR (CDCl₃) δ 55.322, 113.127, 127.508, 128.130, 129.214, 129.252, 130.147, 134.364, 135.988, 175.133.

Table 2 shows the structures and the properties of the compounds that were synthesized by the above examples.

TABLE 2

| | | | | |
|---|---|---|---|---|
| | | | ClogP | Property |
| | 348.36 | 30 mg | 2.57 | Soluble in 10% DMSO (1 mg/mL) |
| 4a | 409.52 | 30 mg | 6.65 | Soluble in 10% DMSO (20 μg/mL) |

TABLE 2-continued

The structures and the properties of Compounds in Examples

| | | | ClogP | Property |
|---|---|---|---|---|
| 4b | 325.36 | 30 mg | 4.60 | Soluble in 10% DMSO (100 μg/mL) |
| 4c | 359.81 | 30 mg | 5.19 | Soluble in 10% DMSO (100 μg/mL) |
| 4d | 359.81 | 30 mg | 5.59 | Soluble in 10% DMSO (100 μg/mL) |
| 4e | 359.81 | 30 mg | 5.59 | Soluble in 10% DMSO (100 μg/mL) |
| 4f | 393.36 | 30 mg | 5.97 | Soluble in 10% DMSO (100 μg/mL) |

TABLE 2-continued

The structures and the properties of Compounds in Examples

| 출발물질 | 분자량 | 시료량/농도 | ClogP | Property |
|---|---|---|---|---|
| 4g | 348.36 | 30 mg | 2.57 | Soluble in 10% DMSO (100 μg/mL) |
| 4h | 343.72 | 30 mg | 3.90 | Soluble in 10% DMSO (100 μg/mL) |
| 4i | 343.72 | 30 mg | 3.90 | Soluble in 10% DMSO (100 μg/mL) |
| 7a | 283.71 | 30 mg | 4.35 | Soluble in 10% DMSO (100 μg/mL) |
| 7b | 318.15 | 30 mg | 4.75 | Soluble in 10% DMSO (100 μg/mL) |

TABLE 2-continued
The structures and the properties of Compounds in Examples
| | | | ClogP | Property |
|---|---|---|---|---|
| 7c | 318.15 | 30 mg | 4.75 | Soluble in 10% DMSO (100 µg/mL) |
| 7d | 318.15 | 30 mg | 5.59 | Soluble in 10% DMSO (100 µg/mL) |
| 4j | 343.35 | 20 mg | 4.848 | Soluble in 10% DMSO (100 µg/mL) |
| 4k | 343.35 | 20 mg | 5.018 | Soluble in 10% DMSO (100 µg/mL) |
| 4l | 343.35 | 20 mg | 5.018 | Soluble in 10% DMSO (100 µg/mL) |
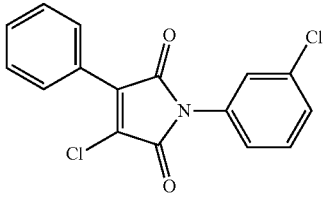
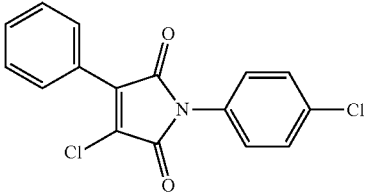
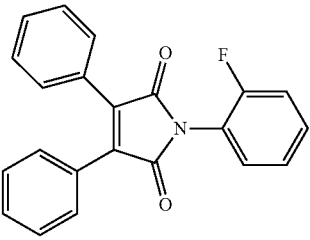
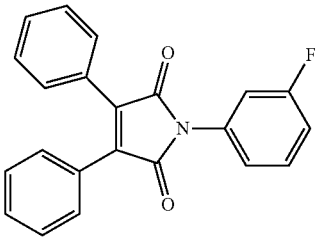
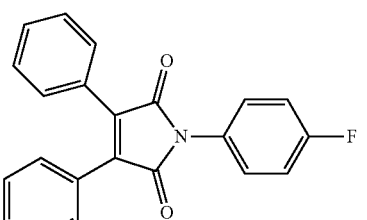

TABLE 2-continued
The structures and the properties of Compounds in Examples
| | | | ClogP | Property |
|---|---|---|---|---|
| 4m | 339.39 | 20 mg | 3.634 | Soluble in 10% DMSO (100 μg/mL) |
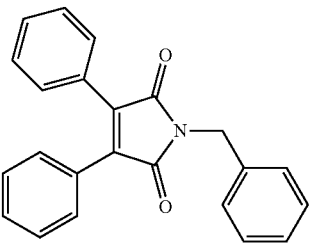
| 4n | 357.38 | 20 mg | 3.777 | Soluble in 10% DMSO (100 μg/mL) |
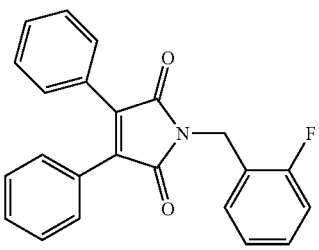
| 4o | 357.38 | 20 mg | 3.777 | Soluble in 10% DMSO (100 μg/mL) |
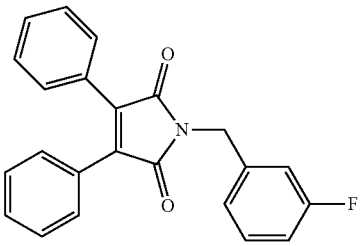
| 4p | 357.38 | 20 mg | 3.777 | Soluble in 10% DMSO (100 μg/mL) |
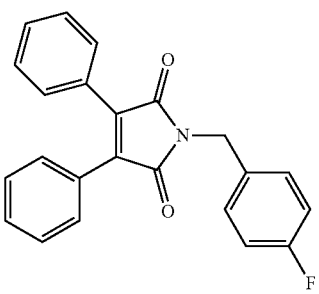
| 4q | 353.41 | 20 mg | 4.263 | Soluble in 10% DMSO (100 μg/mL) |
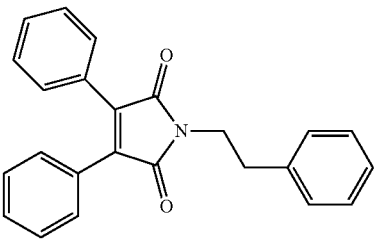

TABLE 2-continued
The structures and the properties of Compounds in Examples
| | | | ClogP | Property |
|---|---|---|---|---|
| 4r | 371.40 | 20 mg | 4.406 | Soluble in 10% DMSO (100 μg/mL) |
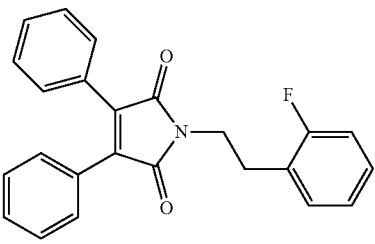
| 4s | 371.40 | 20 mg | 4.406 | Soluble in 10% DMSO (100 μg/mL) |
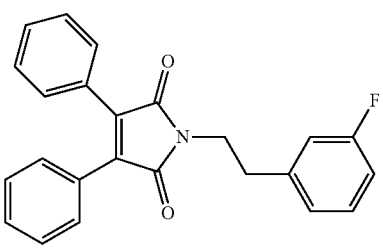
| 4t | 371.40 | 20 mg | 4.406 | Soluble in 10% DMSO (100 μg/mL) |
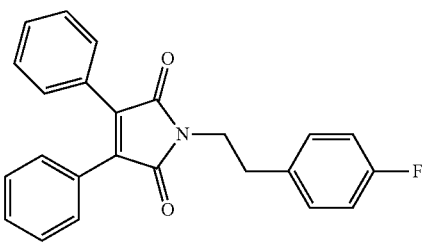
| 17a | 394.25 | 20 mg | 6.301 | Soluble in 10% DMSO (100 μg/mL) |
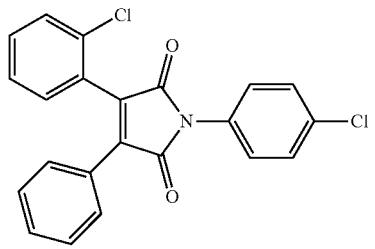
| 17b | 394.25 | 20 mg | 6.301 | Soluble in 10% DMSO (100 μg/mL) |
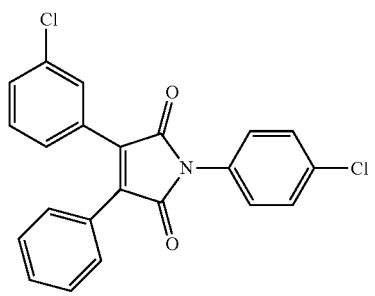

TABLE 2-continued

The structures and the properties of Compounds in Examples

| | | | ClogP | Property |
|---|---|---|---|---|
| 17c | 394.25 | 20 mg | 6.301 | Soluble in 10% DMSO (100 μg/mL) |
| 17d | 428.70 | 20 mg | 7.014 | Soluble in 10% DMSO (100 μg/mL) |
| 8 | 361.82 | 20 mg | 4.9168 | Soluble in 10% DMSO (100 μg/mL) |
| 14 | 345.82 | 20 mg | 6.027 | Soluble in 10% DMSO (100 μg/mL) |
| AJ-3036 | 404.93 | 20 mg | 6.1121 | Soluble in 10% DMSO (100 μg/mL) |

TABLE 2-continued

The structures and the properties of Compounds in Examples

| 화합물 | 분자량 | 치료환 농도 | ClogP | Property |
|---|---|---|---|---|
| 6a | 265.26 | 20 mg | 3.25 | Soluble in 10% DMSO (100 μg/mL) |

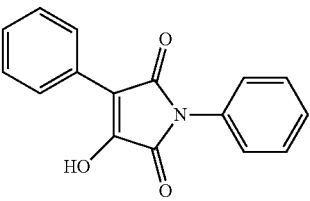

| 17e | 365.84 | 20 mg | 5.9628 | Soluble in 10% DMSO (100 μg/mL) |

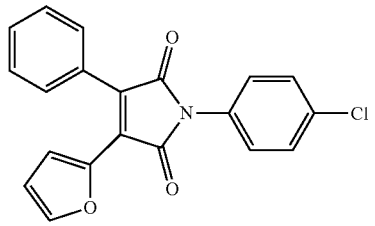

| AJ-3039 | 285.72 | 20 mg | 3.8688 | Soluble in 10% DMSO (100 μg/mL) |

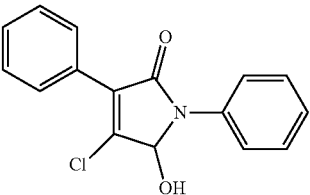

| 21 | 331.84 | 20 mg | 6.3168 | Soluble in DMSO |

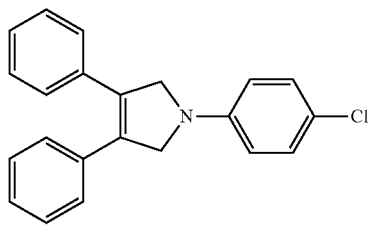

| 23 | 361.82 | 20 mg | 4.372 | Soluble in DMSO |

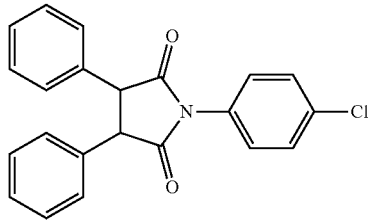

Experimental Example 1

Inhibition Effect on Osteoclast Differentiation

RAW 264.7 cell, a mouse macrophage/monocyte cell line which can be differentiated in various forms depends on its surrounding environments and stimuli, is differentiated to multinucleated osteoclast by the stimulus of RANKL (100 ng/ml). Inhibition effect of each compound on osteoclast differentiation was analyzed by comparing the degree of osteoclast differentiation when RAW 264.7 cell was treated with RANKL and the subject each compound simultaneously.

The experiment procedures were more specifically described as follows:

Inhibition activities of osteoclast differentiation in respect of compounds 4a, 4b, 4c, 4d, 4e, 4f, 4 g, 4 h, 4i, 4j, 4k, 4l, 4m, 4n, 4o, 7a, 7b, 7c, and 7d were tested. Macrophage/monocyte RAW 264.7 cell was used as a cell and $1.5 \times 10^3$ cells were seeded in a 96 well plate. The synthesized compound and zoledronic acid as a control material were dissolved in 10% DMSO aqueous solution and treated to cells according to each concentration (0.5M, 1M, 5M and 10M).

After pre-treating each compound for 6 hours and then, treating RANKL, the incubation was carried out for 7 days in a 5% $CO_2$ incubator. To observe osteoclasts well, they were stained by TRAP (tartrate resistance acid phosphatase) stain method. The number of cells differentiated to osteoclasts was counted and then, a comparative analysis was conducted for the degree of each compound's osteoclast differentiation. The results were shown in the following table 3:

TABLE 3

Results of osteoclast differentiation degrees of the compounds by concentration.

| compounds | 0.5 μM | | 1 μM | | 5 μM | | 10 μM | |
|---|---|---|---|---|---|---|---|---|
| control | 51.5 | | 51.5 | | 51.5 | | 51.5 | |
| ZA | 21 | 58 | 20 | 57 | 25 | 27 | 12 | 20 |
| 4a | 4 | 17 | 13 | 29 | 20 | 57 | 50 | 92 |
| 4b | 29 | 39 | 18 | 30 | 14 | 25 | 16 | 43 |
| 4c | 23 | 35 | 26 | 16 | 13 | 17 | 18 | 26 |
| 4d | 50 | 45 | 38 | 33 | 27 | 34 | 13 | 37 |
| 4e | 23 | 26 | 21 | 29 | 9 | 10 | 7 | 9 |
| 4f | 23 | 26 | 21 | 29 | 9 | 10 | 7 | 9 |
| 4g | 34 | 24 | 48 | 23 | 19 | 26 | 30 | 49 |
| 4h | 48 | 39 | 45 | 38 | 37 | 28 | 31 | 15 |
| 4i | 14 | 28 | 21 | 43 | 27 | 31 | 33 | 49 |
| 4j | 23 | 22 | 45 | 23 | 29 | 42 | 21 | 35 |
| 4k | 40 | — | 25 | — | 40 | — | 28 | — |
| 4l | 7 | 18 | 14 | 22 | 9 | 42 | 24 | 25 |
| 4m | 19 | 27 | 11 | 16 | 30 | 56 | 12 | 24 |
| 4n | 15 | 13 | 23 | 18 | 14 | 24 | 52 | 55 |
| 4o | 21 | 32 | 26 | 20 | 41 | 29 | 33 | 26 |
| 7a | 18 | 29 | 10 | 31 | 31 | 24 | 37 | 38 |
| 7b | 41 | 24 | 24 | 29 | 40 | 44 | 39 | 35 |
| 7c | 26 | 18 | 13 | 15 | 32 | 20 | 27 | 24 |
| 7d | 12 | 21 | 28 | 29 | 22 | 40 | 24 | 27 |

Figure 2:
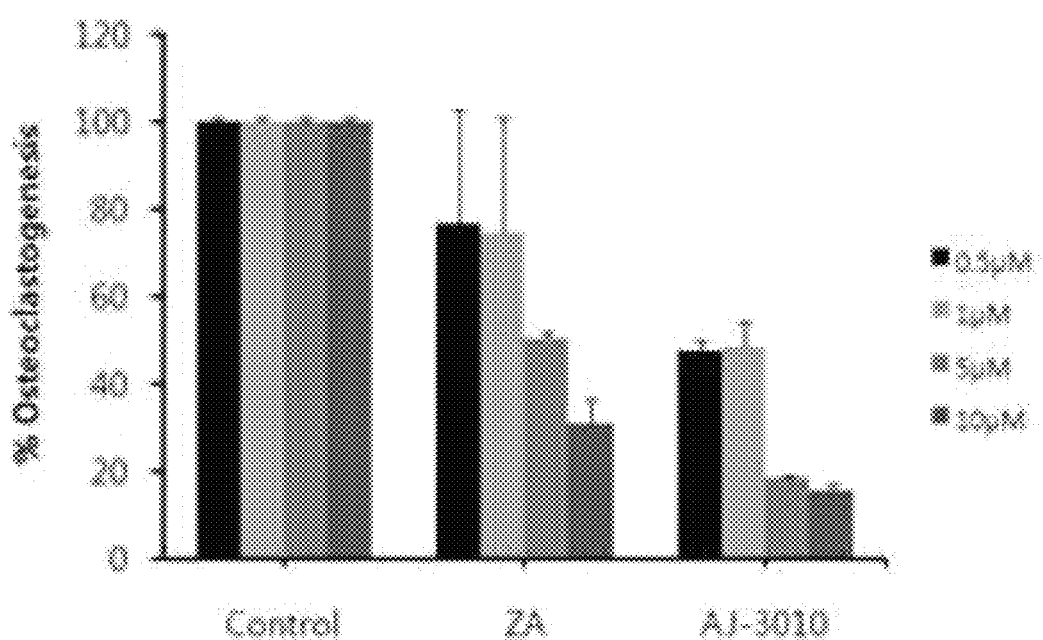
FIG. 2 depicts the dose-dependent inhibitory effect on osteoclast differentiation by treating RAW 264.7 cells with the compounds of the invention, zoledronic acid in a graph.

Only the osteoclasts containing nucleus number more than 4 were only counted as effective analysis targets in both control and experiment groups (See FIGS. 1 and 2).

As the results, all synthetic compounds showed the inhibition effects on osteoclast differentiation. Especially, compound 4e showed more superior inhibition effect on osteoclast differentiation than the control group of zoledronic acid.

Experimental Example 2

Inhibition of NF-kappa B

Figure 3:
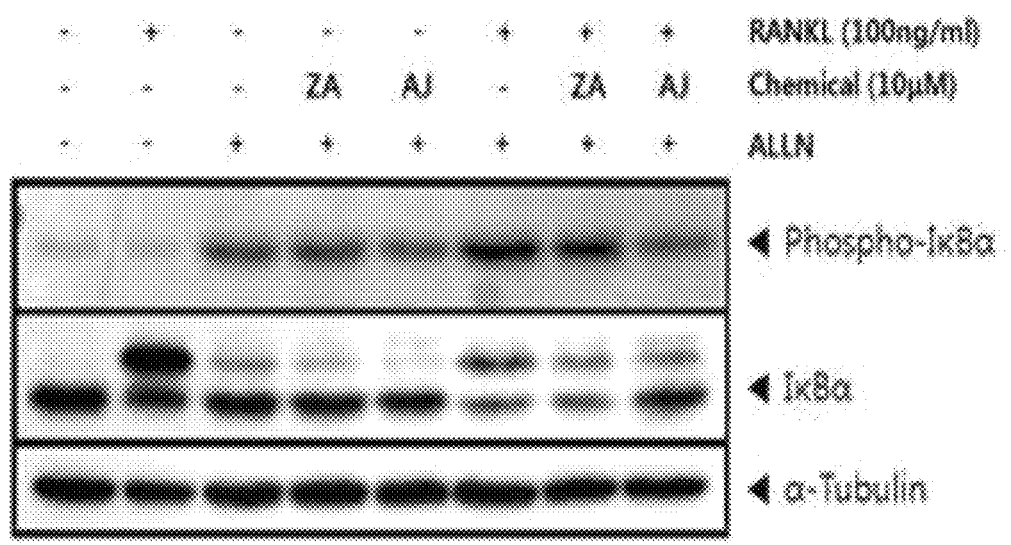
FIG. 3 depicts the inhibitory effect on NF-κB transcription when administering the compound of invention and zoledronic acid.

The compound 4e showed relatively high inhibition effect of the differentiation of osteoclasts and the control zolendronic acid (ZA) group were comparatively analyzed for the regulation function of NF-kappa B. After the concentration of 10 μM ZA and 10 μM compound 4e were treated to RAW264.7 cells for 12 hours, ALLN (protease inhibitors, 50 μg/ml) and RANKL were continuously treated for 30 minutes respectively. It is confirmed that the compound of 4e is suppressed the mechanism of NF-kappa B 2 times more than ZA (FIG. 3)

Experimental Example 3

Analysis of Inhibition Activity of RANK Receptor Binding

Figure 4:
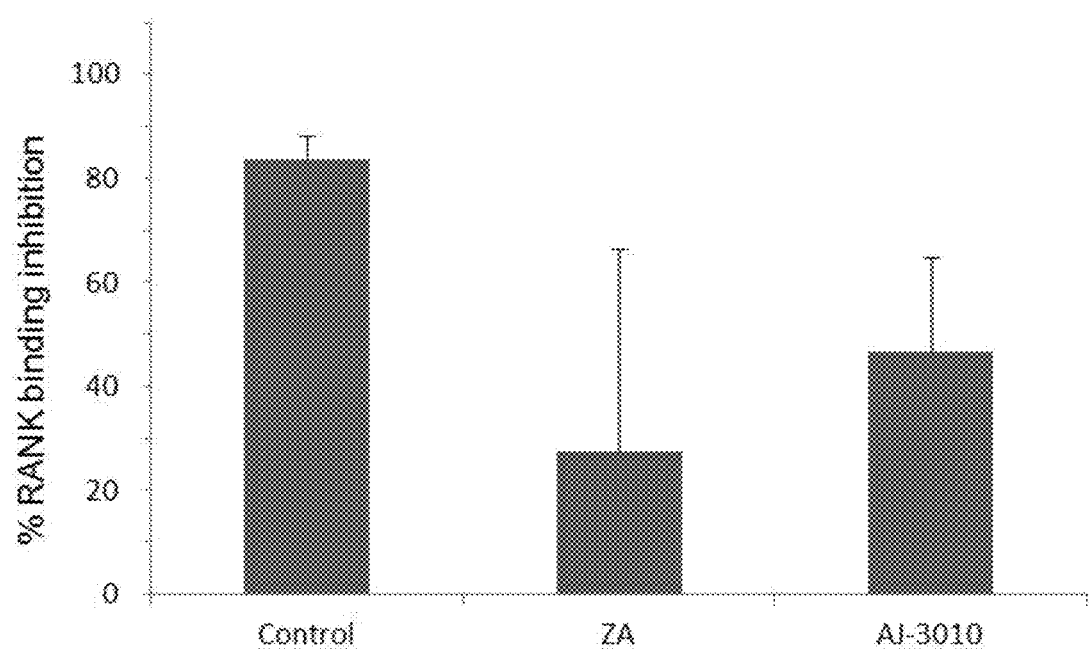
FIG. 4 depicts the inhibitory effect on the binding of RNAKL with RANK receptor when administering the compound of invention and zoledronic acid.

After the human recombinant sRNAK receptor molecule (100 μg/ml, PeproTech) was fixed to the protein chip (PeproTech), human recombinant sRANK ligand (10 μg/ml, PeproTech) was treated and incubated for 1 hour. OPG molecule was used as a positive control, and the compound and OPG are simultaneously treated. A comparative analysis was conducted to compare the binding inhibition effect of the compound using OPG as a control. Mouse anti-human sRANK ligand monoclonal antibody coupled with Cy5-fluorescent (1.0 μg/ml, PeproTech) was treated for 30 minutes, and scanning the strength of luminescence by using image analysis scanner and analyzed to the GraphPad Prism 4 software. Out of the above stated compounds, compound 4e and ZA were comparatively analyzed. The binding inhibitory activity upon to RANK receptor of the positive control was 83.65% and that of ZA was 27.55%. That of the compound 4e was 46.70%. The binding inhibitory activity upon to the RANK receptor of compound 4e showed superior about 1.7 times to that of ZA (n=6)(FIG. 4)

Experimental Example 4

Analysis of Inhibition Activity of Osteopontin-Integrin Binding

Osteopontin (OPN) molecule is the one of bone phosphoproteins and acts as an important factor of bone remodeling. The OPN provides a role of that integrin molecule of osteoclasts can be attached to the bone inorganic matrix with inducing osteoclasts to develop the formation of tight junction to the bone surface (i.e., ruffled borders), and thus, it can initiate the bone resorption eventually.

Figure 5:
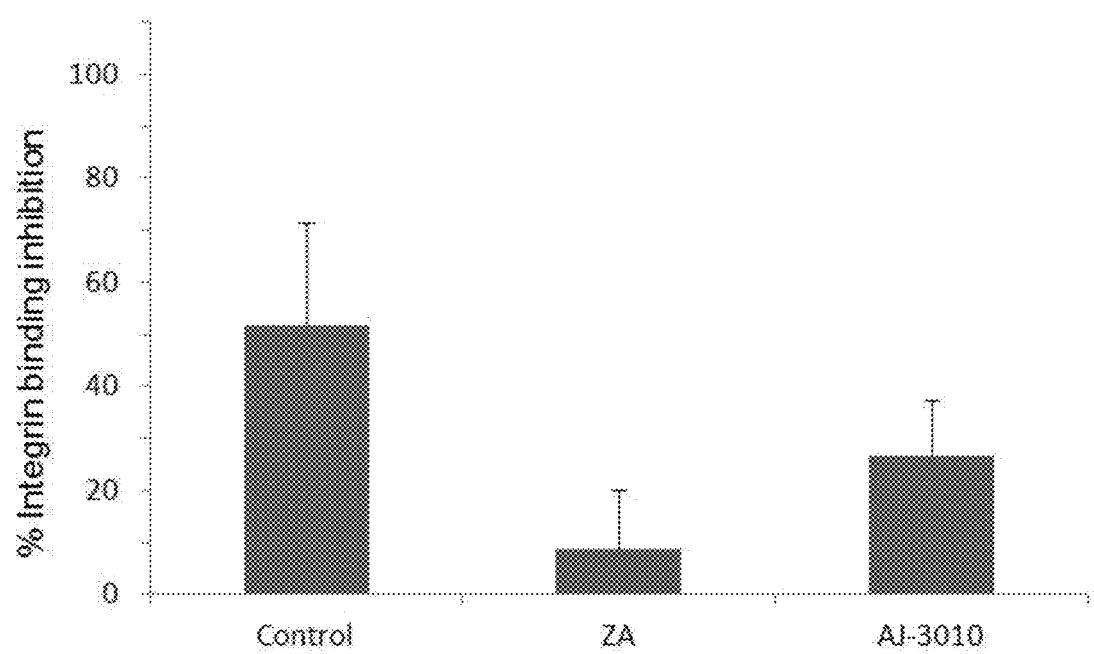
FIG. 5 depicts the inhibitory effect on the binding of osteoclast with bone matrix when administering the compound of invention and zoledronic acid.

After the human integrin $\alpha_v\beta_3$ (100 μg/ml, Milipore) was fixed to the protein chip (PeproTech), the human recombinant OPN (40 μg/ml, PeproTech) molecule coupled with Cy5-fluorescent was reacted for 1 hour. Echistatin molecule (40 μg/ml, Sigma-Aldrich) was used as a positive control. The samples were simultaneously treated to conduct a comparative analysis for the binding inhibitory effect thereof. Finally, the strength of luminescence is scanned by using image analysis scanner and analyzed to the GraphPad Prism 4 software. The binding inhibitory rate of the positive control with ingegrin molecule was 51.75%, that of ZA was 8.65%, and that of compound 4e was 26.45%. The binding inhibitory activity of compound 4e of the invention was about 3 times higher than that of ZA (n=6)(FIG. 5).

Preparation Example 1

The Preparation of the Powder Form

| | |
|---|---|
| Compound 4e | 10 mg |
| Sucrose | 100 mg |
| Talc | 10 mg |

The above ingredients were mixed and filled in packs to obtain the powder form.

Preparation Example 2

The Preparation of the Tablet Form

| | |
|---|---|
| Compound 4e | 10 mg |
| Starch | 100 mg |
| Sucrose | 100 mg |
| Magnesium Stearate | 2 mg |

The above ingredients were mixed and the mixture was formulated into tablets.

Preparation Example 3

The Preparation of the Capsule Form

| | |
|---|---|
| Compound 4e | 10 mg |
| Crystalline Celluose | 3 mg |
| Lactose | 15 mg |
| Magnesium Stearate | 1 mg |

The above ingredients were mixed and the mixture was formulated into capsules by using gelatin capsule.

Preparation Example 4

The Preparation of the Granule Form

| | |
|---|---|
| Compound 4e | 10 mg |
| Soybean extracts | 50 mg |
| Glucose | 200 mg |
| Starch | 500 mg |

The above ingredients were mixed, 100 mL of 30% ethanol was added and dried in 60° C. to formulate granules.

Preparation Example 5

The Preparation of the Pill Form

| | |
|---|---|
| Compound 4e | 20 mg |
| Lactose | 1,500 mg |
| Glycerin | 1,500 mg |
| Starch | 980 mg |

The above ingredients were mixed and the mixture was formulated into pills by using conventional methods. The weight of one pill was 4 g.

Preparation Example 6

The Preparation of the Injection

| | |
|---|---|
| Compound 4e | 10 mg |
| Mannitol | 180 mg |

-continued

| | |
|---|---|
| Sterile distilled water for injection | 2,970 mg |
| Na$_2$HPO$_4$12H$_2$O | 30 mg |

The above ingredients were mixed and the mixture was formulated into injection by using conventional methods. The volume of each of the ampules was 2 mL.

Preparation Example 7

The Preparation of the Solution

| | |
|---|---|
| Compound 4e | 10 mg |
| Isomerized glucose syrup | 10,000 mg |
| Mannitol | 5,000 mg |
| Purified water | Properly |

The above ingredients were mixed and dissolved into the purified water by using conventional methods. Proper flavoring agent was added to the above mixture and sterilized to formulated into solutions.

What is claimed is:

1. A method of treating metabolic bone disease, the method comprising: single or multiple administration of a pharmaceutical composition comprising the compound selected from the group consisting of:
   1-(2,6-diisopropylphenyl)-3,4-diphenyl-1H-pyrrole-2,5-dione;
   1,3,4-triphenyl-1H-pyrrole-2,5-dione;
   1-(2-chlorophenyl)-3,4-diphenyl-1H-pyrrole-2,5-dione;
   1-(3-chlorophenyl)-3,4-diphenyl-1H-pyrrole-2,5-dione;
   1-(4-chlorophenyl)-3,4-diphenyl-1H-pyrrole-2,5-dione;
   3,4-diphenyl-1-(2-(trifluoromethyl)phenyl)-1H-pyrrole-2,5-dione;
   1-cyclohexyl-3,4-diphenyl-1H-pyrrole-2,5-dione;
   4-(2,5-dioxo-3,4-diphenyl-2,5-dihydro-1H-pyrrol-1-yl)-2-hydroxybenzoic acid;
   5-(2,5-dioxo-3,4-diphenyl-2,5-dihydro-1H-pyrrol-1-yl)-2-hydroxybenzoic acid;
   3-chloro-1,4-diphenyl-1H-pyrrole-2,5-dione;
   3-chloro-1-(2-chlorophenyl)-4-phenyl-1H-pyrrole-2,5-dione;
   3-chloro-1-(3-chlorophenyl)-4-phenyl-1H-pyrrole-2,5-dione;
   3-chloro-1-(4-chlorophenyl)-4-phenyl-1H-pyrrole-2,5-dione;
   1-(2-fluorophenyl)-3,4-diphenyl-1H-pyrrole-2,5-dione;
   1-(3-fluorophenyl)-3,4-diphenyl-1H-pyrrole-2,5-dione;
   1-(4-fluorophenyl)-3,4-diphenyl-1H-pyrrole-2,5-dione;
   1-benzyl-3,4-diphenyl-1H-pyrrole-2,5-dione;
   1-(2-fluorobenzyl)-3,4-diphenyl-1H-pyrrole-2,5-dione;
   1-(3-fluorobenzyl)-3,4-diphenyl-1H-pyrrole-2,5-dione;
   1-(4-fluorobenzyl)-3,4-diphenyl-1H-pyrrole-2,5-dione;
   1-phenethyl-3,4-diphenyl-1H-pyrrole-2,5-dione;
   1-(2-fluorophenethyl)-3,4-diphenyl-1H-pyrrole-2,5-dione;
   1-(3-fluorophenethyl)-3,4-diphenyl-1H-pyrrole-2,5-dione;
   1-(4-fluorophenethyl)-3,4-diphenyl-1H-pyrrole-2,5-dione;
   3-(2-chlorophenyl)-1-(4-chlorophenyl)-4-phenyl-1H-pyrrole-2,5-dione;
   3-(3-chlorophenyl)-1-(4-chlorophenyl)-4-phenyl-1H-pyrrole-2,5-dione;

1,3-bis(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrol-2(5H)-one;
1-(4-chlorophenyl)-3,4-diphenyl-1H-pyrrol-2(5H)-one;
1-(4-chlorophenyl)-3-((dimethylamino)methyl)-3,4-diphenylpyrrolidin-2-one;
3-hydroxy-1,4-diphenyl-1H-pyrrole-2,5-dione;
1-(4-chlorophenyl)-3-phenyl-4-(thiophen-2-yl)-1H-pyrrole-2,5-dione;
4-chloro-5-hydroxy-1,3-diphenyl-1H-pyrrol-2(5H)-one; and
1-(4-chlorophenyl)-3,4-diphenyl-2,5-dihydro-1H-pyrrole;
or pharmaceutically acceptable salts thereof,
wherein the metabolic bone disease is selected from the group consisting of bone metastatic cancer, solid cancer bone metastasis, musculoskeletal complication by solid cancer bone metastasis, hypercalcemia by malignant tumor, multiple myeloma, primary bone tumor, osteoporosis, Rheumatoid Arthritis, Osteoarthritis, Periodontal Disease, inflammatory resorption of alveolar bone, inflammatory resorption of bone and Paget's disease.

2. The method of treating metabolic bone disease according to claim 1, the pharmaceutical composition comprising the compound selected from the group consisting of
1-(4-chlorophenyl)-3,4-diphenyl-1H-pyrrole-2,5-dione;
4-(2,5-dioxo-3,4-diphenyl-2,5-dihydro-1H-pyrrol-1-yl)-2-hydroxybenzoic acid;
5-(2,5-dioxo-3,4-diphenyl-2,5-dihydro-1H-pyrrol-1-yl)-2-hydroxybenzoic acid;
3-chloro-1-(2-chlorophenyl)-4-phenyl-1H-pyrrole-2,5-dione;
3-chloro-1-(3-chlorophenyl)-4-phenyl-1H-pyrrole-2,5-dione;
1-(2-fluorophenyl)-3,4-diphenyl-1H-pyrrole-2,5-dione;
1-(3-fluorophenyl)-3,4-diphenyl-1H-pyrrole-2,5-dione;
1-(2-fluorobenzyl)-3,4-diphenyl-1H-pyrrole-2,5-dione;
1-(3-fluorobenzyl)-3,4-diphenyl-1H-pyrrole-2,5-dione;
1-(4-fluorobenzyl)-3,4-diphenyl-1H-pyrrole-2,5-dione;
1-(2-fluorophenethyl)-3,4-diphenyl-1H-pyrrole-2,5-dione;
1-(3-fluorophenethyl)-3,4-diphenyl-1H-pyrrole-2,5-dione;
1-(4-fluorophenethyl)-3,4-diphenyl-1H-pyrrole-2,5-dione;
3-(2-chlorophenyl)-1-(4-chlorophenyl)-4-phenyl-1H-pyrrole-2,5-dione;
3-(3-chlorophenyl)-1-(4-chlorophenyl)-4-phenyl-1H-pyrrole-2,5-dione;
1-(4-chlorophenyl)-3-(2,6-dichlorophenyl)-4-phenyl-1H-pyrrole-2,5-dione;
1-(4-chlorophenyl)-5-hydroxy-3,4-diphenyl-1H-pyrrol-2(5H)-one;
1-(4-chlorophenyl)-3-((dimethylamino)methyl)-3,4-diphenylpyrrolidin-2-one;
1-(4-chlorophenyl)-3-phenyl-4-(thiophen-2-yl)-1H-pyrrole-2,5-dione; and
4-chloro-5-hydroxy-1,3-diphenyl-1H-pyrrol-2(5H)-one,
or pharmaceutically acceptable salts thereof.

3. The method of treating metabolic bone disease according to claim 1, the pharmaceutical composition comprising 1-(4-chlorophenyl)-3,4-diphenyl-1H-pyrrole-2,5-dione as an active ingredient.

* * * * *